United States Patent
Nebosky et al.

(10) Patent No.: US 9,561,354 B2
(45) Date of Patent: Feb. 7, 2017

(54) DRUG DELIVERY IMPLANTS

(71) Applicant: SMed-TA/TD, LLC, Columbia City, IN (US)

(72) Inventors: Paul S. Nebosky, Fort Wayne, IN (US);
Sarah L. Zimmerman, Columbia City, IN (US); Gregory C. Stalcup, Columbia City, IN (US); Troy D. Knapp, Alachua, FL (US)

(73) Assignee: SMed-TA/TD, LLC, Columbia City, IN (US)

( * ) Notice: Subject to any disclaimer, the term of this patent is extended or adjusted under 35 U.S.C. 154(b) by 90 days.

(21) Appl. No.: 14/505,144

(22) Filed: Oct. 2, 2014

(65) Prior Publication Data
US 2015/0038941 A1    Feb. 5, 2015

Related U.S. Application Data

(62) Division of application No. 12/540,676, filed on Aug. 13, 2009, now abandoned.
(Continued)

(51) Int. Cl.
*A61F 2/30* (2006.01)
*A61M 31/00* (2006.01)
(Continued)

(52) U.S. Cl.
CPC ............ *A61M 31/002* (2013.01); *A61B 17/56* (2013.01); *A61B 17/60* (2013.01); *A61B 17/80* (2013.01);
(Continued)

(58) Field of Classification Search
CPC ...... A61M 31/002; A61B 17/56; A61B 17/60; A61B 17/80; A61F 2/30; A61F 2/34; A61F 2/36
(Continued)

(56) References Cited

U.S. PATENT DOCUMENTS

| | | |
|---|---|---|
| 3,662,405 A | 5/1972 | Bortz et al. |
| 3,683,421 A | 8/1972 | Martinie |
| 3,855,638 A | 12/1974 | Pilliar |
| 3,867,728 A | 2/1975 | Stubstad et al. |
| 4,011,602 A | 3/1977 | Rybicki et al. |
| 4,060,081 A | 11/1977 | Yannas et al. |
| 4,156,943 A | 6/1979 | Collier |
| 4,222,128 A | 9/1980 | Tomonaga et al. |

(Continued)

FOREIGN PATENT DOCUMENTS

| | | |
|---|---|---|
| DE | 4211345 C1 | 11/1993 |
| DE | 4423020 A1 | 1/1996 |

(Continued)

OTHER PUBLICATIONS

Office Action dated Jan. 5, 2010 in U.S. Appl. No. 11/060,377 (10 pages).
(Continued)

*Primary Examiner* — Alvin Stewart
(74) *Attorney, Agent, or Firm* — Taylor IP, P.C.

(57) ABSTRACT

An orthopedic implant system includes an external fixation device implantable at a selected location within a corporeal body and configured for delivering at least one therapeutic agent to the corporeal body. The external fixation device includes an implantable pin, a sheath coupled with the pin, a reservoir coupled with the sheath and a plurality of channels. The pin defines the plurality of channels. The reservoir is configured for receiving the at least one therapeutic agent. The plurality of channels are configured for conveying the at least one therapeutic agent from the reservoir to a treatment site relative to the corporeal body.

20 Claims, 9 Drawing Sheets

Related U.S. Application Data

(60) Provisional application No. 61/088,379, filed on Aug. 13, 2008.

(51) Int. Cl.
| | | |
|---|---|---|
| *A61B 17/56* | (2006.01) | |
| *A61B 17/60* | (2006.01) | |
| *A61B 17/80* | (2006.01) | |
| *A61B 17/86* | (2006.01) | |
| *A61F 2/34* | (2006.01) | |
| *A61F 2/36* | (2006.01) | |
| *A61B 17/70* | (2006.01) | |
| *A61B 17/84* | (2006.01) | |
| *A61F 2/40* | (2006.01) | |
| *A61M 5/142* | (2006.01) | |

(52) U.S. Cl.
CPC ........... *A61B 17/864* (2013.01); *A61B 17/866* (2013.01); *A61B 17/8625* (2013.01); *A61F 2/30* (2013.01); *A61F 2/34* (2013.01); *A61F 2/36* (2013.01); *A61B 17/7061* (2013.01); *A61B 17/846* (2013.01); *A61F 2/40* (2013.01); *A61F 2002/3068* (2013.01); *A61F 2002/3092* (2013.01); *A61F 2002/30672* (2013.01); *A61F 2002/30677* (2013.01); *A61F 2002/30714* (2013.01); *A61F 2002/30784* (2013.01); *A61F 2250/0068* (2013.01); *A61F 2250/0089* (2013.01); *A61M 5/14276* (2013.01)

(58) Field of Classification Search
USPC ......... 623/18.11, 22.12, 23.15, 23.19, 22.13; 604/513, 272, 175; 606/315, 301, 304
See application file for complete search history.

(56) References Cited

U.S. PATENT DOCUMENTS

| | | | |
|---|---|---|---|
| 4,274,163 A * | 6/1981 | Malcom | A61B 17/8808 606/94 |
| 4,450,150 A | 5/1984 | Sidman | |
| 4,453,537 A | 6/1984 | Spitzer | |
| 4,485,097 A | 11/1984 | Bell | |
| 4,520,821 A | 6/1985 | Schmidt et al. | |
| 4,608,052 A | 8/1986 | Van Kampen et al. | |
| 4,609,551 A | 9/1986 | Caplan et al. | |
| 4,620,327 A | 11/1986 | Caplan et al. | |
| 4,644,627 A | 2/1987 | Palazzo | |
| 4,660,755 A | 4/1987 | Farling et al. | |
| 4,737,411 A | 4/1988 | Graves, Jr. et al. | |
| 4,769,041 A | 9/1988 | Morscher | |
| 4,846,834 A | 7/1989 | Von Recum et al. | |
| 4,858,603 A | 8/1989 | Clemow et al. | |
| 4,892,550 A * | 1/1990 | Huebsch | A61F 2/4637 623/23.19 |
| 4,936,859 A | 6/1990 | Morscher et al. | |
| 4,976,738 A | 12/1990 | Frey et al. | |
| 5,030,233 A | 7/1991 | Ducheyne | |
| 5,041,107 A | 8/1991 | Heil, Jr. | |
| 5,084,051 A | 1/1992 | Tormala et al. | |
| 5,092,898 A | 3/1992 | Bekki et al. | |
| 5,100,392 A | 3/1992 | Orth et al. | |
| 5,104,410 A | 4/1992 | Chowdhary | |
| 5,116,377 A * | 5/1992 | Skripitz | A61F 2/30728 623/23.19 |
| 5,133,772 A * | 7/1992 | Hack | A61F 2/36 623/23.19 |
| 5,190,550 A | 3/1993 | Miller et al. | |
| 5,197,985 A | 3/1993 | Caplan et al. | |
| 5,204,055 A | 4/1993 | Sachs et al. | |
| 5,219,363 A | 6/1993 | Crowninshield et al. | |
| 5,226,914 A | 7/1993 | Caplan et al. | |
| 5,281,210 A | 1/1994 | Burke et al. | |
| 5,282,861 A | 2/1994 | Kaplan | |
| 5,290,291 A * | 3/1994 | Linden | A61B 17/8847 606/86 R |
| 5,306,309 A | 4/1994 | Wagner et al. | |
| 5,328,765 A | 7/1994 | Anderson et al. | |
| 5,340,362 A * | 8/1994 | Carbone | A61F 2/30723 606/95 |
| 5,370,690 A | 12/1994 | Barrett | |
| 5,376,123 A * | 12/1994 | Klaue | A61B 17/8841 623/23.19 |
| 5,380,328 A | 1/1995 | Morgan | |
| 5,443,471 A | 8/1995 | Swajger | |
| 5,458,643 A | 10/1995 | Oka et al. | |
| 5,462,362 A | 10/1995 | Yuhta et al. | |
| 5,490,962 A | 2/1996 | Cima et al. | |
| 5,496,372 A | 3/1996 | Hamamoto et al. | |
| 5,514,182 A | 5/1996 | Shea | |
| 5,518,680 A | 5/1996 | Cima et al. | |
| 5,531,750 A | 7/1996 | Even-Esh | |
| 5,534,028 A | 7/1996 | Bao et al. | |
| 5,537,851 A | 7/1996 | Sheu et al. | |
| 5,549,700 A | 8/1996 | Graham et al. | |
| 5,571,187 A | 11/1996 | Devanathan | |
| 5,593,443 A | 1/1997 | Carter et al. | |
| 5,637,175 A | 6/1997 | Feygin et al. | |
| 5,641,323 A | 6/1997 | Caldarise | |
| 5,702,446 A * | 12/1997 | Schenck | A61F 2/30907 433/226 |
| 5,702,449 A | 12/1997 | McKay | |
| 5,730,817 A | 3/1998 | Feygin et al. | |
| 5,732,469 A | 3/1998 | Hamamoto et al. | |
| 5,750,103 A | 5/1998 | Cherksey | |
| 5,769,897 A | 6/1998 | Haerle | |
| 5,776,199 A | 7/1998 | Michelson | |
| 5,800,828 A | 9/1998 | Dionne et al. | |
| 5,807,406 A | 9/1998 | Brauker et al. | |
| 5,848,989 A | 12/1998 | Villani | |
| 5,849,015 A | 12/1998 | Haywood et al. | |
| 5,869,170 A | 2/1999 | Cima et al. | |
| 5,871,484 A | 2/1999 | Spievack et al. | |
| 5,876,550 A | 3/1999 | Feygin et al. | |
| 5,879,406 A | 3/1999 | Lilley | |
| 5,916,269 A | 6/1999 | Serbousek et al. | |
| 5,960,797 A * | 10/1999 | Kramer | A61B 17/3472 128/898 |
| 5,971,985 A | 10/1999 | Carchidi et al. | |
| 5,989,250 A | 11/1999 | Wagner et al. | |
| 6,010,336 A | 1/2000 | Shimotoso et al. | |
| 6,045,581 A | 4/2000 | Burkinshaw | |
| 6,066,154 A * | 5/2000 | Reiley | A61B 17/7097 606/192 |
| 6,110,179 A | 8/2000 | Flivik et al. | |
| 6,136,029 A | 10/2000 | Johnson et al. | |
| 6,136,031 A | 10/2000 | Middleton | |
| 6,139,574 A | 10/2000 | Vacanti et al. | |
| 6,143,035 A | 11/2000 | McDowell | |
| 6,159,247 A | 12/2000 | Klawitter et al. | |
| 6,176,874 B1 | 1/2001 | Vacanti et al. | |
| 6,238,435 B1 | 5/2001 | Meulink et al. | |
| 6,283,997 B1 | 9/2001 | Garg et al. | |
| 6,290,726 B1 | 9/2001 | Pope et al. | |
| 6,306,424 B1 | 10/2001 | Vyakarnam et al. | |
| 6,315,797 B1 | 11/2001 | Middleton | |
| 6,322,564 B1 | 11/2001 | Surma | |
| 6,333,029 B1 | 12/2001 | Vyakarnam et al. | |
| 6,337,198 B1 | 1/2002 | Levene et al. | |
| 6,365,149 B2 | 4/2002 | Vyakarnam et al. | |
| 6,379,391 B1 | 4/2002 | Masini | |
| 6,395,011 B1 | 5/2002 | Johanson et al. | |
| 6,409,764 B1 | 6/2002 | White et al. | |
| 6,419,704 B1 | 7/2002 | Ferree | |
| 6,423,095 B1 | 7/2002 | Van Hoeck et al. | |
| 6,423,252 B1 | 7/2002 | Chun et al. | |
| 6,425,921 B1 | 7/2002 | Grundei et al. | |
| 6,440,734 B1 | 8/2002 | Pykett et al. | |
| 6,454,811 B1 | 9/2002 | Sherwood et al. | |
| 6,461,385 B1 | 10/2002 | Gayer et al. | |
| 6,471,689 B1 | 10/2002 | Joseph et al. | |
| 6,471,993 B1 | 10/2002 | Shastri et al. | |

(56) References Cited

U.S. PATENT DOCUMENTS

| | | | |
|---|---|---|---|
| 6,475,137 B1* | 11/2002 | Elist | A61F 2/26 600/40 |
| 6,491,666 B1* | 12/2002 | Santini, Jr. | A61F 2/91 128/899 |
| 6,494,916 B1 | 12/2002 | Babalola et al. | |
| 6,514,514 B1 | 2/2003 | Atkinson et al. | |
| 6,520,993 B2 | 2/2003 | James et al. | |
| 6,526,984 B1 | 3/2003 | Nilsson et al. | |
| 6,527,810 B2 | 3/2003 | Johnson et al. | |
| 6,530,958 B1 | 3/2003 | Cima et al. | |
| 6,533,818 B1 | 3/2003 | Weber et al. | |
| 6,534,084 B1 | 3/2003 | Vyakarnam et al. | |
| 6,544,472 B1 | 4/2003 | Compton et al. | |
| 6,547,824 B1 | 4/2003 | Price | |
| 6,551,290 B1 | 4/2003 | Elsberry et al. | |
| 6,554,857 B1 | 4/2003 | Zilla et al. | |
| 6,565,572 B2 | 5/2003 | Chappius | |
| 6,571,130 B1 | 5/2003 | Ljungstroem et al. | |
| 6,599,322 B1 | 7/2003 | Amrich et al. | |
| 6,610,095 B1 | 8/2003 | Pope et al. | |
| 6,626,950 B2 | 9/2003 | Brown et al. | |
| 6,635,049 B1 | 10/2003 | Robinson et al. | |
| 6,645,251 B2 | 11/2003 | Salehi et al. | |
| 6,656,489 B1 | 12/2003 | Mahmood et al. | |
| 6,660,040 B2 | 12/2003 | Chan et al. | |
| 6,673,108 B2 | 1/2004 | Zilla et al. | |
| 6,682,567 B1 | 1/2004 | Schroeder | |
| 6,692,528 B2 | 2/2004 | Ward et al. | |
| 6,709,463 B1 | 3/2004 | Pope et al. | |
| 6,709,464 B2 | 3/2004 | Scott et al. | |
| 6,712,850 B2 | 3/2004 | Vyakarnam et al. | |
| 6,723,120 B2 | 4/2004 | Yan | |
| 6,736,850 B2 | 5/2004 | Davis | |
| 6,740,120 B1* | 5/2004 | Grimes | A61B 17/1659 623/22.12 |
| 6,749,636 B2 | 6/2004 | Michelson | |
| 6,758,863 B2 | 7/2004 | Estes et al. | |
| 6,783,546 B2 | 8/2004 | Zuckerman et al. | |
| 6,818,620 B2 | 11/2004 | Bhatnagar | |
| 6,852,272 B2 | 2/2005 | Artz et al. | |
| 6,863,899 B2 | 3/2005 | Koblish et al. | |
| 6,866,685 B2 | 3/2005 | Chan et al. | |
| 6,881,413 B1 | 4/2005 | Bartholeyns | |
| 6,893,465 B2 | 5/2005 | Huang | |
| 6,913,623 B1 | 7/2005 | Zhu | |
| 6,916,321 B2 | 7/2005 | TenHuisen et al. | |
| 6,958,078 B2 | 10/2005 | Goel et al. | |
| 6,969,383 B2 | 11/2005 | Hildebrand | |
| 6,979,336 B2* | 12/2005 | Durniak | A61B 17/8802 606/92 |
| 6,979,353 B2 | 12/2005 | Bresina | |
| 6,989,033 B1 | 1/2006 | Schmidt | |
| 6,993,406 B1 | 1/2006 | Cesarano, III et al. | |
| 7,018,416 B2 | 3/2006 | Hanson et al. | |
| 7,018,418 B2 | 3/2006 | Amrich et al. | |
| 7,052,710 B2 | 5/2006 | Giordano et al. | |
| 7,077,867 B1 | 7/2006 | Pope et al. | |
| 7,087,086 B2 | 8/2006 | Li et al. | |
| 7,087,200 B2 | 8/2006 | Taboas et al. | |
| 7,090,668 B1* | 8/2006 | U | A61K 9/0024 604/892.1 |
| 7,094,371 B2 | 8/2006 | Lo | |
| 7,108,828 B2 | 9/2006 | Lefebvre et al. | |
| 7,112,223 B2 | 9/2006 | Davis | |
| 7,128,762 B2 | 10/2006 | Middleton | |
| 7,174,282 B2 | 2/2007 | Hollister et al. | |
| 7,189,409 B2 | 3/2007 | Pirhonen et al. | |
| 7,192,440 B2 | 3/2007 | Andreas et al. | |
| 7,208,222 B2 | 4/2007 | Rolfe et al. | |
| 7,226,612 B2 | 6/2007 | Sohier et al. | |
| 7,238,186 B2 | 7/2007 | Zdeblick et al. | |
| 7,238,363 B2 | 7/2007 | Mansouri et al. | |
| 7,250,055 B1* | 7/2007 | Vanderwalle | A61B 17/7098 606/71 |
| 7,250,060 B2 | 7/2007 | Trieu | |
| 7,255,713 B2 | 8/2007 | Malek | |
| 7,300,439 B2 | 11/2007 | May | |
| 7,354,452 B2 | 4/2008 | Foley | |
| 7,537,617 B2 | 5/2009 | Bindsell et al. | |
| 7,537,664 B2 | 5/2009 | O'Neill et al. | |
| 7,575,572 B2 | 8/2009 | Sweeney | |
| 7,632,228 B2 | 12/2009 | Brauker et al. | |
| 7,632,338 B2 | 12/2009 | Cipollini | |
| 7,666,230 B2 | 2/2010 | Orban et al. | |
| 7,674,426 B2 | 3/2010 | Grohowski, Jr. | |
| 7,674,477 B1 | 3/2010 | Schmid et al. | |
| 7,717,956 B2 | 5/2010 | Lang | |
| 7,875,080 B2 | 1/2011 | Puno et al. | |
| 7,892,290 B2* | 2/2011 | Bergin | A61F 2/30734 623/23.22 |
| 8,454,706 B2* | 6/2013 | de Beaubien | A61F 2/36 623/23.39 |
| 8,475,505 B2* | 7/2013 | Nebosky | A61B 17/7061 606/304 |
| 8,500,819 B2* | 8/2013 | Meridew | A61F 2/3662 604/48 |
| 8,900,322 B2* | 12/2014 | de Beaubien | A61F 2/36 623/23.39 |
| 8,900,323 B2* | 12/2014 | de Beaubien | A61F 2/36 623/23.39 |
| 2001/0038848 A1 | 11/2001 | Donda et al. | |
| 2001/0039455 A1 | 11/2001 | Simon et al. | |
| 2002/0022884 A1 | 2/2002 | Mansmann | |
| 2002/0029083 A1 | 3/2002 | Zucherman et al. | |
| 2002/0035400 A1 | 3/2002 | Bryan et al. | |
| 2002/0062154 A1 | 5/2002 | Ayers | |
| 2002/0072798 A1 | 6/2002 | Riesle et al. | |
| 2002/0091447 A1 | 7/2002 | Shimp et al. | |
| 2002/0106393 A1 | 8/2002 | Bianchi et al. | |
| 2002/0128715 A1 | 9/2002 | Bryan et al. | |
| 2002/0143402 A1 | 10/2002 | Steinberg | |
| 2002/0161447 A1 | 10/2002 | Salehi et al. | |
| 2002/0182241 A1 | 12/2002 | Borenstein et al. | |
| 2002/0183850 A1 | 12/2002 | Felt et al. | |
| 2002/0197178 A1 | 12/2002 | Yan | |
| 2003/0003127 A1 | 1/2003 | Brown et al. | |
| 2003/0004578 A1 | 1/2003 | Brown et al. | |
| 2003/0006534 A1 | 1/2003 | Taboas et al. | |
| 2003/0012805 A1 | 1/2003 | Chen et al. | |
| 2003/0023311 A1 | 1/2003 | Trieu | |
| 2003/0055506 A1 | 3/2003 | Stoy et al. | |
| 2003/0060886 A1 | 3/2003 | Van Hoeck et al. | |
| 2003/0060891 A1* | 3/2003 | Shah | A61F 2/30728 623/22.13 |
| 2003/0069465 A1 | 4/2003 | Benkowski et al. | |
| 2003/0097182 A1 | 5/2003 | Buchman et al. | |
| 2003/0097184 A1* | 5/2003 | Mitsugi | A61B 17/8802 623/23.19 |
| 2003/0105527 A1 | 6/2003 | Bresina | |
| 2003/0114934 A1 | 6/2003 | Steinberg | |
| 2003/0114936 A1 | 6/2003 | Sherwood et al. | |
| 2003/0118649 A1 | 6/2003 | Gao et al. | |
| 2003/0120344 A1 | 6/2003 | Michelson | |
| 2003/0130743 A1 | 7/2003 | Scott et al. | |
| 2003/0139809 A1 | 7/2003 | Worst | |
| 2003/0171738 A1* | 9/2003 | Konieczynski | A61M 5/14276 604/891.1 |
| 2003/0171820 A1 | 9/2003 | Wilshaw et al. | |
| 2003/0180171 A1 | 9/2003 | Artz et al. | |
| 2003/0187513 A1* | 10/2003 | Durniak | A61B 17/8802 623/22.12 |
| 2003/0203002 A1 | 10/2003 | Murphy et al. | |
| 2003/0206928 A1 | 11/2003 | Tormala et al. | |
| 2003/0208274 A1 | 11/2003 | Davis | |
| 2004/0024470 A1 | 2/2004 | Giordano et al. | |
| 2004/0034357 A1 | 2/2004 | Beane et al. | |
| 2004/0034427 A1 | 2/2004 | Goel et al. | |
| 2004/0063206 A1 | 4/2004 | Rowley et al. | |
| 2004/0073197 A1 | 4/2004 | Kim | |
| 2004/0115172 A1 | 6/2004 | Bianchi et al. | |
| 2004/0126405 A1 | 7/2004 | Sahatjian et al. | |
| 2004/0147905 A1 | 7/2004 | Krumme | |

(56) References Cited

U.S. PATENT DOCUMENTS

| | | |
|---|---|---|
| 2004/0153165 A1 | 8/2004 | Li et al. |
| 2004/0180072 A1* | 9/2004 | Tunc ................ A61F 2/30721 424/423 |
| 2004/0191106 A1 | 9/2004 | O'Neill et al. |
| 2004/0191292 A1 | 9/2004 | Chou |
| 2004/0193273 A1 | 9/2004 | Huang |
| 2004/0199260 A1 | 10/2004 | Pope et al. |
| 2004/0210274 A1 | 10/2004 | Bauhahn et al. |
| 2004/0210316 A1 | 10/2004 | King et al. |
| 2004/0215173 A1* | 10/2004 | Kunst ................ A61M 5/14244 604/891.1 |
| 2004/0225360 A1 | 11/2004 | Malone |
| 2004/0249463 A1 | 12/2004 | Bindseil et al. |
| 2004/0265350 A1 | 12/2004 | Sambrook et al. |
| 2004/0267263 A1 | 12/2004 | May |
| 2005/0015059 A1 | 1/2005 | Sweeney |
| 2005/0015150 A1* | 1/2005 | Lee ................ A61F 2/442 623/17.12 |
| 2005/0021084 A1 | 1/2005 | Lu et al. |
| 2005/0049715 A1 | 3/2005 | Ito et al. |
| 2005/0049716 A1 | 3/2005 | Wagener et al. |
| 2005/0055099 A1 | 3/2005 | Ku |
| 2005/0058684 A1 | 3/2005 | Shanley et al. |
| 2005/0059972 A1 | 3/2005 | Biscup |
| 2005/0085888 A1 | 4/2005 | Andreas et al. |
| 2005/0100470 A1 | 5/2005 | Lefebvre et al. |
| 2005/0100578 A1 | 5/2005 | Schmid et al. |
| 2005/0112397 A1 | 5/2005 | Rolfe et al. |
| 2005/0119753 A1 | 6/2005 | McGahan et al. |
| 2005/0125073 A1 | 6/2005 | Orban et al. |
| 2005/0137707 A1 | 6/2005 | Malek |
| 2005/0143822 A1 | 6/2005 | Paul |
| 2005/0159819 A1 | 7/2005 | McCormack et al. |
| 2005/0171611 A1 | 8/2005 | Stoy et al. |
| 2005/0175703 A1 | 8/2005 | Hunter et al. |
| 2005/0177238 A1 | 8/2005 | Khandkar et al. |
| 2005/0177247 A1 | 8/2005 | Canham et al. |
| 2005/0182494 A1 | 8/2005 | Schmid |
| 2005/0187555 A1 | 8/2005 | Biedermann et al. |
| 2005/0192669 A1 | 9/2005 | Zdeblick et al. |
| 2005/0197654 A1 | 9/2005 | Edman et al. |
| 2005/0202371 A1 | 9/2005 | McGuire |
| 2005/0220837 A1 | 10/2005 | Disegi et al. |
| 2005/0222688 A1 | 10/2005 | Zilla et al. |
| 2005/0228503 A1 | 10/2005 | Gundolf |
| 2005/0246032 A1 | 11/2005 | Bokros et al. |
| 2005/0271694 A1 | 12/2005 | Mansouri et al. |
| 2005/0272153 A1 | 12/2005 | Xuenong et al. |
| 2005/0273082 A1 | 12/2005 | Olsen |
| 2005/0273178 A1 | 12/2005 | Boyan et al. |
| 2006/0002810 A1 | 1/2006 | Grohowski, Jr. |
| 2006/0015186 A1 | 1/2006 | Isaac |
| 2006/0047341 A1* | 3/2006 | Trieu ................ A61F 2/442 623/17.12 |
| 2006/0057737 A1 | 3/2006 | Santini, Jr. et al. |
| 2006/0064170 A1 | 3/2006 | Smith et al. |
| 2006/0064172 A1 | 3/2006 | Trieu |
| 2006/0083730 A1 | 4/2006 | Kusanagi et al. |
| 2006/0093646 A1* | 5/2006 | Cima ................ A61C 8/0012 424/425 |
| 2006/0100706 A1* | 5/2006 | Shadduck ......... A61B 17/1617 623/17.11 |
| 2006/0100716 A1 | 5/2006 | Lerf |
| 2006/0105015 A1 | 5/2006 | Perla et al. |
| 2006/0111782 A1 | 5/2006 | Petersen |
| 2006/0111785 A1 | 5/2006 | O'Neil |
| 2006/0121609 A1 | 6/2006 | Yannas et al. |
| 2006/0129242 A1 | 6/2006 | Bergeron et al. |
| 2006/0141012 A1 | 6/2006 | Gingras |
| 2006/0149220 A1 | 7/2006 | Ullestad et al. |
| 2006/0149386 A1 | 7/2006 | Clarke et al. |
| 2006/0173542 A1 | 8/2006 | Shikinami |
| 2006/0178744 A1 | 8/2006 | de Villiers et al. |
| 2006/0193885 A1 | 8/2006 | Leonard Neethling et al. |
| 2006/0195188 A1 | 8/2006 | O'Driscoll et al. |
| 2006/0204581 A1 | 9/2006 | Gower et al. |
| 2006/0229715 A1 | 10/2006 | Istephanous et al. |
| 2006/0235534 A1 | 10/2006 | Gertzman et al. |
| 2006/0241593 A1 | 10/2006 | Sherman et al. |
| 2006/0264950 A1 | 11/2006 | Nelson et al. |
| 2006/0271022 A1 | 11/2006 | Steinbach et al. |
| 2006/0271201 A1 | 11/2006 | Kumar et al. |
| 2006/0276900 A1 | 12/2006 | Carpenter |
| 2006/0282166 A1 | 12/2006 | Molz et al. |
| 2006/0287689 A1* | 12/2006 | Debruyne ............ A61K 9/0046 607/57 |
| 2006/0289388 A1 | 12/2006 | Yang et al. |
| 2006/0293757 A1 | 12/2006 | McKay et al. |
| 2007/0016163 A1* | 1/2007 | Santini, Jr. ........... A61C 8/0012 604/500 |
| 2007/0026069 A1 | 2/2007 | Shastri et al. |
| 2007/0038299 A1 | 2/2007 | Stone et al. |
| 2007/0041952 A1 | 2/2007 | Guilak et al. |
| 2007/0043446 A1 | 2/2007 | Murray |
| 2007/0077267 A1 | 4/2007 | Molz, IV et al. |
| 2007/0105222 A1 | 5/2007 | Wolfinbarger et al. |
| 2007/0116734 A1 | 5/2007 | Akash |
| 2007/0123843 A1* | 5/2007 | Gill ................ A61M 5/14232 604/890.1 |
| 2007/0138042 A1 | 6/2007 | Wood |
| 2007/0141105 A1 | 6/2007 | Stein et al. |
| 2007/0141533 A1 | 6/2007 | Ford et al. |
| 2007/0150063 A1 | 6/2007 | Ruberte et al. |
| 2007/0150064 A1 | 6/2007 | Ruberte et al. |
| 2007/0150068 A1 | 6/2007 | Dong et al. |
| 2007/0160681 A1 | 7/2007 | Park et al. |
| 2007/0161986 A1 | 7/2007 | Levy |
| 2007/0162110 A1 | 7/2007 | Dave |
| 2007/0166348 A1 | 7/2007 | Van Dyke |
| 2007/0168021 A1 | 7/2007 | Holmes et al. |
| 2007/0185580 A1 | 8/2007 | Posel |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0202145 A1 | 8/2007 | Ghabrial et al. |
| 2007/0203584 A1 | 8/2007 | Bandyopadhyay et al. |
| 2007/0208420 A1 | 9/2007 | Ameer et al. |
| 2007/0233071 A1 | 10/2007 | Dewey et al. |
| 2007/0243225 A1 | 10/2007 | McKay |
| 2007/0250169 A1 | 10/2007 | Lang |
| 2007/0255262 A1* | 11/2007 | Haase ................ A61M 5/14276 604/891.1 |
| 2007/0255416 A1 | 11/2007 | Melkent et al. |
| 2007/0260320 A1 | 11/2007 | Peterman et al. |
| 2007/0270859 A1 | 11/2007 | Companioni et al. |
| 2007/0293948 A1 | 12/2007 | Bagga et al. |
| 2008/0004704 A1 | 1/2008 | Katz |
| 2008/0015578 A1 | 1/2008 | Erickson et al. |
| 2008/0046082 A1 | 2/2008 | Lee |
| 2008/0065218 A1 | 3/2008 | O'Neil |
| 2008/0077247 A1 | 3/2008 | Murillo et al. |
| 2008/0109083 A1 | 5/2008 | Van Hoeck et al. |
| 2008/0119945 A1 | 5/2008 | Frigg |
| 2008/0147193 A1 | 6/2008 | Matthis et al. |
| 2008/0188940 A1 | 8/2008 | Cohen et al. |
| 2008/0200985 A1 | 8/2008 | Robie |
| 2008/0262622 A1 | 10/2008 | Butler |
| 2008/0288074 A1 | 11/2008 | O'Neil et al. |
| 2008/0306609 A1 | 12/2008 | Lee et al. |
| 2009/0005872 A1 | 1/2009 | Moumene et al. |
| 2009/0005874 A1 | 1/2009 | Fleischmann et al. |
| 2009/0024224 A1 | 1/2009 | Chen et al. |
| 2009/0030399 A1* | 1/2009 | Raiszadeh ............ A61F 2/441 604/506 |
| 2009/0069899 A1* | 3/2009 | Klein ................ A61F 2/36 623/22.4 |
| 2009/0132051 A1 | 5/2009 | Moskowitz et al. |
| 2009/0192493 A1* | 7/2009 | Meng ................ A61F 9/0017 604/513 |
| 2009/0222098 A1 | 9/2009 | Trieu et al. |
| 2009/0228109 A1 | 9/2009 | Pointillant et al. |
| 2009/0248162 A1 | 10/2009 | Peckham |

(56) References Cited

U.S. PATENT DOCUMENTS

| | | | |
|---|---|---|---|
| 2009/0254182 A1 | 10/2009 | Kovarik et al. | |
| 2009/0270986 A1 | 10/2009 | Christensen | |
| 2009/0270988 A1 | 10/2009 | Snell et al. | |
| 2009/0270991 A1 | 10/2009 | Michelson | |
| 2009/0270992 A1 | 10/2009 | Gerber et al. | |
| 2009/0276049 A1 | 11/2009 | Weiland | |
| 2009/0281517 A1 | 11/2009 | Lambrecht et al. | |
| 2009/0281625 A1 | 11/2009 | Enayati | |
| 2009/0292363 A1 | 11/2009 | Goldfarb et al. | |
| 2009/0326657 A1 | 12/2009 | Grinberg et al. | |
| 2010/0003639 A1 | 1/2010 | Salvi et al. | |
| 2010/0016970 A1 | 1/2010 | Kapitan et al. | |
| 2010/0042167 A1* | 2/2010 | Nebosky | A61B 17/7061 606/315 |
| 2010/0042213 A1* | 2/2010 | Nebosky | A61B 17/56 623/16.11 |
| 2010/0042214 A1* | 2/2010 | Nebosky | A61B 17/56 623/16.11 |
| 2010/0042215 A1* | 2/2010 | Stalcup | A61B 17/68 623/16.11 |
| 2010/0042218 A1 | 2/2010 | Nebosky et al. | |
| 2010/0042226 A1 | 2/2010 | Nebosky et al. | |
| 2010/0076559 A1 | 3/2010 | Bagga et al. | |
| 2010/0190254 A1 | 7/2010 | Chian et al. | |
| 2010/0234966 A1 | 9/2010 | Lo | |
| 2010/0291286 A1 | 11/2010 | O'Neill et al. | |
| 2011/0064784 A1 | 3/2011 | Mullens et al. | |
| 2011/0153028 A1 | 6/2011 | Albertorio | |
| 2011/0218644 A1* | 9/2011 | Meridew | A61F 2/3662 623/23.15 |
| 2015/0038941 A1* | 2/2015 | Nebosky | A61B 17/56 604/506 |
| 2015/0238691 A1* | 8/2015 | Boyden | A61F 2/30 604/66 |

FOREIGN PATENT DOCUMENTS

| | | |
|---|---|---|
| DE | 693 28 047 T2 | 3/2000 |
| DE | 19904436 A1 | 8/2000 |
| DE | 10051438 A1 | 5/2002 |
| DE | 695 28 346 T2 | 9/2002 |
| DE | 10120330 A1 | 11/2002 |
| DE | 10157315 C1 | 8/2003 |
| EP | 0617931 A2 | 10/1994 |
| EP | 0827726 A2 | 3/1998 |
| EP | 1 273 312 A2 | 1/2003 |
| EP | 1 287 851 A1 | 3/2003 |
| EP | 1475057 A1 | 11/2004 |
| EP | 1806112 A1 | 7/2007 |
| FR | 2697155 A1 | 4/1994 |
| JP | 6007388 A | 1/1994 |
| JP | 7116184 A | 5/1995 |
| JP | 8173463 A | 7/1996 |
| JP | 2587625 B2 | 12/1996 |
| JP | 2002325781 A | 11/2002 |
| JP | 2005329179 A | 12/2005 |
| WO | 03026714 A1 | 4/2003 |
| WO | 03084602 A2 | 10/2003 |
| WO | 03101504 A1 | 12/2003 |
| WO | 2005/047467 A2 | 5/2005 |
| WO | 2006/088480 A2 | 8/2006 |
| WO | 2006/135727 A2 | 12/2006 |
| WO | 2007/135444 A2 | 11/2007 |

OTHER PUBLICATIONS

Office Action dated Sep. 24, 2010 in U.S. Appl. No. 11/060,377 (7 pages).
A. Cameron, entitled "Basic Lubrication Theory", Ellis Horwood Limited, pp. 134-137, 1976.
A. Cameron, entitled "The Principles of Lubrication", John Wiley and Sons Inc., pp. 542-559, 1966.
Office Action dated May 12, 2010 in U.S. Appl. No. 10/980,425 (22 pages).
Philip E. Mitchell, Handbook Editor, "Tool and Manufacturing Engineers Handbook", 4th Edition, vol. VIII Plastic Part Manufacturing, Society of Manufacturing Engineers, Dearborn, Michigan, pp. 2-17 and 2-18, 1996 (4 pages).
U.S. Appl. No. 60/149,027, filed Aug. 16, 1999 with U.S. Patent & Trademark Office (44 pages).
U.S. Appl. No. 08/200,636, filed Feb. 23, 1994 with U.S. Patent & Trademark Office (40 pages).
Office Action dated Apr. 17, 1995 in U.S. Appl. No. 08/200,636 (4 pages).
Supplemental Information Disclosure Statement dated Sep. 11, 1995 in U.S. Appl. No. 08/200,636 (7 pages).
U.S. Appl. No. 08/437,781, filed May 9, 1995 with U.S. Patent & Trademark Office (84 pages).
Office Action dated Nov. 1, 1996 in U.S. Appl. No. 08/437,781 (2 pages).
U.S. Appl. No. 09/639,612, filed Aug. 15, 2000 with U.S. Patent & Trademark Office (67 pages).
International Preliminary Report on Patentability dated Feb. 15, 2011 for PCT/US2009/053724 (9 pages).
International Preliminary Report on Patentability dated Feb. 15, 2011 for PCT/US2009/053735 (8 pages).
International Preliminary Report on Patentability dated Feb. 15, 2011 for PCT/US2009/053751 (7 pages).
International Preliminary Report on Patentability dated Feb. 15, 2011 for PCT/US2009/053762 (5 pages).
International Preliminary Report on Patentability dated Mar. 1, 2011 for PCT/US2009/055380 (9 pages).
International Preliminary Report on Patentability dated Mar. 1, 2011 for PCT/US2009/055397 (10 pages).
Communication dated Apr. 11, 2013 from Canadian Intellectual Property Office for Canadian patent application No. 2,735,236 (3 pages).
Communication dated May 22, 2013 from European Patent Office for European Patent Application No. 09807307.5-1506 (1 page).
Communication dated May 2, 2013 from European Patent Office for European Patent Application No. 09807307.5-1506, including Supplementary European Search Report and opinion (7 pages).
Communication from Canadian Intellectual Property Office dated Jan. 11, 2013 for Canadian patent application No. 2,735,235 (2 pages).
Extended European Search Report dated Apr. 17, 2014 for European Application No. 09 80 7295 (5 pages).
PCT/US2009/053724 International Search Report dated Sep. 28, 2009.
International Search Report dated Sep. 28, 2009 of International Searching Authority for Application No. PCT/US2009/053724 (2 pages).
International Search Report dated Sep. 28, 2009 of International Searching Authority for Application No. PCT/US2009/053735 (2 pages).
International Search Report dated Sep. 23, 2009 of International Searching Authority for Application No. PCT/US2009/053762 (2 pages).
International Search Report dated Oct. 14, 2009 of International Searching Authority for Application No. PCT/US2009/053751 (2 pages).
International Search Report dated Apr. 13, 2010 of International Searching Authority for Application No. PCT/US2009/055380 (2 pages).
International Search Report dated Oct. 13, 2009 of International Searching Authority for Application No. PCT/US2009/055397 (2 pages).
Office Action dated Oct. 9, 2007 in U.S. Appl. No. 10/980,425 (16 pages).
Office Action dated Apr. 7, 2008 in U.S. Appl. No. 10/980,425 (20 pages).
Office Action dated Jul. 17, 2008 in U.S. Appl. No. 10/980,425 (3 pages).
Office Action dated Oct. 29, 2008 in U.S. Appl. No. 11/325,530 (11 pages).

(56) References Cited

OTHER PUBLICATIONS

Office Action dated Jun. 26, 2009 in U.S. Appl. No. 11/325,530 (13 pages).
Office Action dated Oct. 19, 2009 in U.S. Appl. No. 11/325,530 (6 pages).
Robert J. Klebe; article entitled "Cytoscribing: A Method for Micropositioning Cells and the Construction of Two- and Three-Dimensional Synthetic Tissues", Experimental Cell Research 179 (1988) 362-373, published by Academic Press, Inc.
Emanuel Sachs, Michael Cima, James Bredt, Alain Curodeau, Tailin Fan, and David Brancazio; article entitled "Cad-Casting: Direct Fabrication of Ceramic Shells and Cores by Three Dimensional Printing", Manufacturing Review vol. 5, No. 2, pp. 117-126, Jun. 1992, published by American Society of Mechanical Engineers.
Joseph P. Vacanti, Martin A. Morse, W. Mark Saltzman, Abraham J. Domb, Antonio Perez-Atayde, and Robert Langer; article entitled "Selective Cell Transplantation Using Bioabsorbable Artificial Polymers as Matrices", Journal of Pediatric Surgery, vol. 23, No. 1, pp. 3-9, Jan. 1988, published by Grune & Stratton, Inc.
N.R. Boeree, J. Dove, J.J. Cooper, J. Knowles, and G.W. Hastings, article entitled "Development of a Degradable Composite for Orthopaedic Use: Mechanical Evaluation of an Hydroxyapatite-Polyhydroxybutyrate Composite Material", Biomaterials, vol. 14, No. 10, pp. 793-796, 1993, published by Butterworth-Heinemann Ltd.
R.B. Martin, M.W. Chapman, N.A. Sharkey, S.L. Zissimos, B. Bay, and E.C. Shors, article entitled "Bone Ingrowth and Mechanical Properties of Coralline Hydroxyapatite 1 Yr After Implantation", Biomaterials, vol. 14, No. 5, pp. 341-348, 1993, published by Butterworth-Heinemann Ltd.
Article entitled "Fractal" (nine pages), published on the Internet by the online encyclopedia Wikipedia; downloaded from the internet on Dec. 14, 2006 in the United States from the following address: http://en.wikipedia.org/wiki/Fractals.
Editor in Chief Sybil P. Parker, p. 799 (showing entries from "fp" to "fracture test") of McGraw-Hill Dictionary of Scientific and Technical Terms, Fifth Edition, published by McGraw-Hill, Inc., 1994, New York.
Office Action dated Oct. 31, 2008 in U.S. Appl. No. 10/980,425 (20 pages).
Office Action dated Oct. 20, 2006 in U.S. Appl. No. 11/060,377 (10 pages).
Written Opinion dated Sep. 28, 2009 of International Searching Authority for Application No. PCT/US2009/053724 (8 pages).
Written Opinion dated Sep. 28, 2009 of International Searching Authority for Application No. PCT/US2009/053735 (7 pages).
Written Opinion dated Sep. 23, 2009 of International Searching Authority for Application No. PCT/US2009/053762 (4 pages).
Written Opinion dated Oct. 14, 2009 of International Searching Authority for Application No. PCT/US2009/053751 (6 pages).
Article entitled "Rolled Threads" (3 pages), published on the Internet by the online encyclopedia Wikipedia; downloaded from the internet on Aug. 24, 2009 in the United States from the following address: http://en.wikipedia.org/wiki/File:American_Machinists_Handbook--2e--p23--v001.png.
Written Opinion dated Apr. 13, 2010 of International Searching Authority for Application No. PCT/US2009/055380 (8 pages).
Written Opinion dated Oct. 13, 2009 of International Searching Authority for Application No. PCT/US2009/055397 (9 pages).
Unknown Author, article entitled "MacroPore Resorbable Technology: An Overview", Scientific Data Series in Resorbable Fixation, MKT004 Rev. 6/01, pp. 1-8; distributed by Medtronic Sofamor Danek, 1800 Pyramid Place, Memphis TN 38132, (Jun. 2001).
Ralph E. Holmes, M.D., Stefan M. Lemperle, M.D., and Christopher J. Calhoun, M.B.A., article entitled "Protected Bone Regeneration", Scientific Data Series in Resorbable Fixation, MKT003 Rev. 6/01, pp. 1-10; distributed by Medtronic Sofamor Danek, 1800 Pyramid Place, Memphis TN 38132, (Jun. 2001).
D.R. Sumner, T.M. Turner, R.M. Urban, R.M. Leven, M. Hawkins, E.H. Nichols, J.M. McPherson, J.O. Galante, article entitled "Locally Delivered rhTGF-B2 Enhances Bone Ingrowth and Bone Regeneration at Local and Remote Sites of Skeletal Injury", Journal of Orthopaedic Research 19 (2001) pp. 85-94, published by Elsevier Science Ltd.
International Search Report dated May 18, 2005 of International Searching Authority for Application No. PCT/US2004/036997 (3 pages).
U.S. Appl. No. 08/048,408, filed Apr. 15, 1993 with U.S. Patent & Trademark Office (108 pages).
Preliminary Amendment dated Jul. 8, 1993 and filed in U.S. Appl. No. 08/048,408 with U.S. Patent & Trademark Office (12 pages).
International Preliminary Report on Patentability dated May 8, 2006 of International Searching Authority for Application No. PCT/US2004/036997 (6 pages).
Written Opinion dated May 18, 2005 of International Searching Authority for Application No. PCT/US2004/036997 (5 pages).
Communication and supplementary European search report dated Nov. 14, 2008 from European Patent Office in application No. 04818642 (3 pages).
Office Action dated Jun. 25, 2010 from European Patent Office in application No. 04818642 (5 pages).
International Search Report dated Mar. 12, 2007 of International Searching Authority for PCT/US2005/019045 (3 pages).
International Preliminary Report on Patentability dated Aug. 21, 2007 of International Searching Authority for Application No. PCT/US2005/019045 (7 pages).
Written Opinion dated Mar. 12, 2007 of International Searching Authority for Application No. PCT/US2005/019045 (6 pages).
Office Action dated May 7, 2007 in U.S. Appl. No. 11/060,377 (13 pages).
Office Action dated Aug. 20, 2007 in U.S. Appl. No. 11/060,377 (3 pages).
Office Action dated Feb. 20, 2008 in U.S. Appl. No. 11/060,377 (5 pages).
Office Action dated Sep. 2, 2008 in U.S. Appl. No. 11/060,377 (7 pages).
Office Action dated Dec. 15, 2008 in U.S. Appl. No. 11/060,377 (8 pages).
Interview Summary dated Mar. 5, 2009 in U.S. Appl. No. 11/060,377 (2 pages).
Office Action dated May 27, 2009 in U.S. Appl. No. 11/060,377 (7 pages).

* cited by examiner

DRUG DELIVERY IMPLANTS

CROSS REFERENCE TO RELATED APPLICATIONS

This is a division of U.S. patent application Ser. No. 12/540,676, entitled "DRUG DELIVERY IMPLANTS," filed Aug. 13, 2009, which is incorporated herein by reference. U.S. patent application Ser. No. 12/540,676 is a non-provisional application based upon U.S. Provisional Patent Application Ser. No. 61/088,379, entitled "DRUG DELIVERY IMPLANTS," filed Aug. 13, 2008, which is incorporated herein by reference.

BACKGROUND OF THE INVENTION

1. Field of the Invention

The present invention relates to implants, and, more particularly, to orthopaedic implants.

2. Description of the Related Art

Orthopaedic implants include short-term implants, long-term implants, and non-permanent implants. Short-term implants include implants for the treatment of infection. Long-term implants include total implants for total hip, knee, shoulder, and elbow joints. Non-permanent implants include trauma products such as nails, plates, and external fixation devices.

Regarding short-term implants, when tissue, especially bone, surrounding an orthopaedic implant becomes infected, that implant must typically be removed, the infection must be eliminated, and a new implant (revision implant) is then implanted. The span of time between implant removal and revision implantation can be from several weeks (about 4 weeks) to a few months (approximately 3 months). During this time surgeons currently have two basic options: create temporary implants during surgery with antibiotic bone cement (created with or without the aid of a mold) or use a preformed antibiotic bone cement temporary implant (e.g. Exactech's InterSpace™ Hip and Knee). In either case, antibiotic bone cement is used to deliver antibiotics directly to the site of the infection in the bone. The patient also typically receives IV antibiotics. The shortcomings of such implants are the limited duration in which they deliver a clinically relevant dose of antibiotics, the lack of ability to change antibiotic type or dose during the 4-12 week treatment time, and the limited patient mobility, range of motion, and weight bearing that they allow.

Further, antibiotic cements typically provide useful local antibiotic levels for a duration of less than one week. The treatment time is frequently 6 to 8 weeks. However, beyond one week, the antibiotic cement implants provide no useful amount of antibiotics.

Further, infections can be caused by a great number of bacteria, viruses, yeast, etc. The effectiveness of various antibiotics depends greatly upon what in particular has caused the infection. Thus, in order to treat an infection most effectively, the cause of that infection must be known. The results of cell cultures give this information and indicate which antibiotic and dose will most effectively treat the infection. The samples for culturing are usually collected during surgery. The results of the culture are not known until several days after the surgery. Since the type of antibiotic cement used in current temporary implants must be chosen at or before the time of surgery, the information gained from the cultures cannot be applied to the antibiotics used at the infection site.

Further, one key to a patient recovering from joint surgery with full range of motion in that joint is to encourage movement of that joint. This helps to prevent the formation of scar tissue and stiffening of tissue around the joint. The current options for temporary implants allow limited range of motion and weight bearing at best.

Regarding long-term implants, with regard to bone ingrowth, bone ingrowth into a porous material is sometimes required to provide stability or fixation of an implant to the bone. Examples of this include porous coatings on total joint components, fusion devices (i.e., spinal fusion devices), and bone augmentation components (i.e., tibial wedges).

With regard to resorbtion, resorbtion can occur in the region surrounding a total joint implant for a number of reasons and can lead to implant loosening and subsequent revision surgery. Some causes of resorbtion include:

Stress shielding—Bone tissue requires loading to remain strong and healthy. If an implant does not properly transfer loads to the surrounding bone, regions of bone can resorb.

Lysis due to wear particles—Osteolysis and resorbtion are frequently caused by the body's reaction to wear particles created by the bearing of one total joint component on another.

Osteoporosis or other bone disorders—bone metabolic disorders can also cause the resorbtion of bone.

With regard to oncology, localized delivery of oncological drugs in the region of tumors may improve results in slowing/halting tumor growth. The ability for localized delivery may also lessen the need/dose of systemic drugs, resulting in fewer side effects.

Regarding non-permanent implants (i.e., trauma implants), such non-permanent implants include nails, plates, and external fixation devices. Nails are temporary, intramedullary devices. They are typically used to treat traumatic fracture. The risk of infection can be high especially in the case of open fractures. With regard to oncology, nails can be used to treat fractures associated with bone tumors. They can also be used to help prevent a fracture where cancer has weakened bone. Plates treat many of the same indications as nails; however plates are applied to the outside of the bone. External fixation devices are a temporary implant that is used to stabilize a fracture. These can be used for days to months. External fixation devices typically include several pins fixed in the bone and extending through the skin to a rigid plate, ring, rod, or similar stabilizing device. These devices carry the added risk of infection due to their extending through the skin. Bacteria can travel along the pins directly to the soft tissue and bone.

What is needed in the art is an orthopaedic implant which includes a reservoir and a plurality of channels leading from the reservoir to deliver at least one therapeutic agent locally to bone or surrounding soft tissue.

SUMMARY OF THE INVENTION

The present invention provides an orthopaedic implant which includes a reservoir and a plurality of channels leading from the reservoir to deliver at least one therapeutic agent locally to bone or surrounding soft tissue.

The invention in one form is directed to an orthopaedic implant system, including an orthopaedic implant implantable at a selected location within a corporeal body and configured for delivering at least one therapeutic agent to the corporeal body. The implant includes a reservoir and a plurality of channels. The reservoir is configured for receiving the at least one therapeutic agent. The plurality of channels are configured for conveying the at least one therapeutic agent from the reservoir to a treatment site relative to the corporeal body.

The invention in another form is directed to a method of using an orthopaedic implant system, the method including the steps of: implanting an orthopaedic implant at a selected location within a corporeal body, the implant including a reservoir and a plurality of channels; receiving at least one therapeutic agent in the reservoir; conveying the at least one therapeutic agent from the reservoir to a treatment site relative to the corporeal body via the plurality of channels; and delivering the at least one therapeutic agent to the corporeal body.

The invention in yet another form is directed to an orthopaedic implant system including an orthopaedic implant and a porous surface. The orthopaedic implant includes a body implantable at a selected location within a corporeal body and which is configured for delivering a therapeutic agent to the corporeal body. The body includes an exterior surface defining a plurality of surface channels and having an absence of a therapeutic agent reservoir. The plurality of surface channels are configured for receiving, holding, delivering, and being refilled with the therapeutic agent after the implant has been implanted in the corporeal body. The porous surface is attached to the exterior surface. The porous surface is configured for receiving at least one of bone and tissue ingrowth therein and includes a first side attached to the exterior surface and a second side opposing the first side. The porous surface includes a plurality of through-holes running from the first side to the second side. The plurality of surface channels communicate and cooperate with the plurality of through-holes to provide the therapeutic agent from the plurality of surface channels to the first side of the porous surface and to the second side of the porous surface.

An advantage of the present invention is that it provides an orthopaedic implant that allows for the delivery of drugs directly to the bone.

Another advantage of the present invention is that it provides a temporary or short-term implant that would allow for the delivery of antibiotics directly to the bone and surrounding tissue.

Yet another advantage of the present invention is that it would allow for post-operative injections of antibiotics into the implant, thereby allowing for the delivery of multiple antibiotics throughout treatment.

Yet another advantage of the present invention is that the implant according to the present invention allows for the delivery of the correct dose of antibiotics, continuously for any length of time required.

Yet another advantage of the present invention is that is provides an orthopaedic implant which can deliver a therapeutic agent locally to bone or surrounding soft tissue as long as the implant remains implanted in a corporeal body.

Yet another advantage of the present invention is that it provides a long-term implant which would allow drugs to be delivered directly to the bone and surrounding tissue (or to any specific location).

Yet another advantage of the present invention is that, with regard to enhancing bone ingrowth and combating resorbtion, it provides that bone growth stimulators can be injected intraoperatively or postoperatively to enhance or speed bone ingrowth into porous material (i.e., porous coatings on total joint components; fusion devices, i.e., spinal fusion devices; bone augmentation components, i.e., tibial wedges); these drugs could also be injected months to years post-operatively, using an implant according to the present invention, to combat bone resorbtion due to such causes as stress-shielding, osteolysis, or bone metabolic disorders.

Yet another advantage of the present invention is that, with regard to oncology, the present invention provides an implant that would similarly allow for delivery of drugs to some or all tissue surrounding the implant.

Yet another advantage of the present invention is that it would allow antibiotics to be delivered to the bone surrounding the nail of the present invention as a preventative or to treat an infection if one develops.

Yet another advantage of the present invention is that it provides a non-permanent implant, such as a nail according to the present invention, which can provide the delivery of bone growth stimulators directly to the region of bone fracture(s); such delivery of bone growth stimulators can be advantageous in difficult cases such as non-unions, bony defects, and osteotomies.

Yet another advantage of the present invention is that it provides a non-permanent implant, such as a nail according to the present invention, which can provide localized delivery of oncological drugs in the region of tumors which may improve results in slowing/halting tumor growth; this ability for localized delivery provided by the present invention may also lessen the need/dose of systemic drugs, resulting in fewer side effects.

Yet another advantage of the present invention is that it provides an external fixation device that would allow antibiotics or other anti-infective agents to be provided to the bone and soft tissue surrounding the pins.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1:
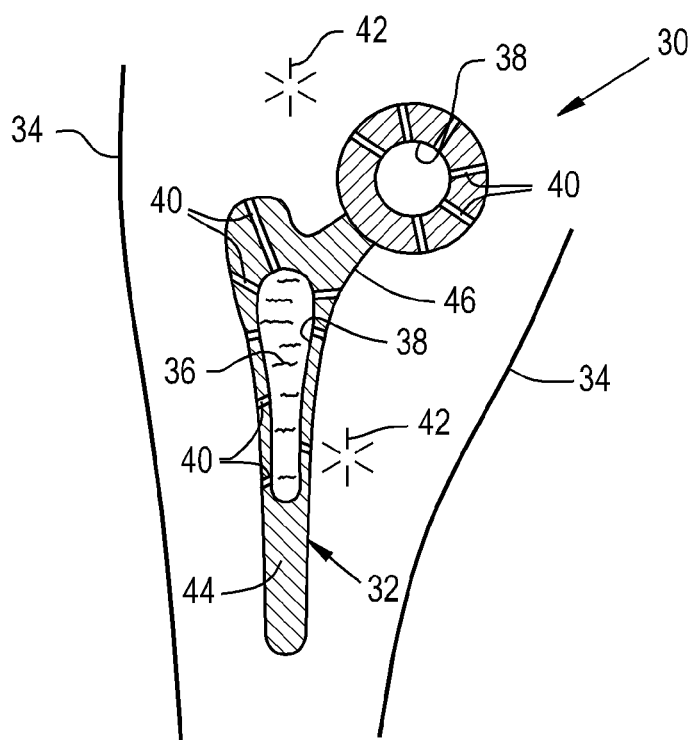
FIG. 1 is a schematic representation of a sectional view of a short-term femoral hip implant according to the present invention.

Referring now to the drawings, and more particularly to FIG. 1, there is shown an orthopaedic implant system 30 according to the present invention which generally includes an orthopaedic implant 32 implantable at a selected location within a corporeal body 34 and configured for delivering at least one therapeutic agent 36 to the corporeal body 34. The implant 32 includes at least one reservoir 38 and a plurality of channels 40. The reservoir 38 is configured for receiving at least one therapeutic agent 36 and can be configured for being refilled with the therapeutic 36 agent after the implant 32 has been implanted in the corporeal body 34. Channels 40 form pathways for the therapeutic agent 36 to move from the reservoir 38 to a treatment site 42 relative to the corporeal body 34. Each pathway formed by a channel 40 is an interior space formed by the walls of channel 40. Channel 40 can, for example, have a circular, square, or some other cross-sectional shape. Thus, channels 40 are configured for conveying at least one therapeutic agent 36 from reservoir 38 to treatment site 42 relative to corporeal body 34.

Figure 3:
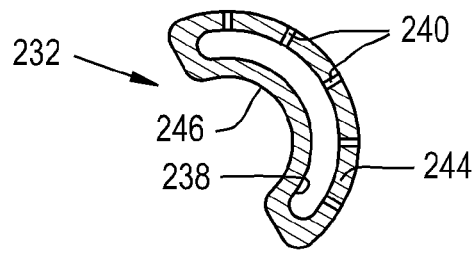
FIG. 3 is a schematic representation of a sectional view of a short-term acetabular cup implant according to the present invention.

FIG. 1 shows two reservoirs 38 and a plurality of channels 40 running from each reservoir 38. The implant according to the present invention (i.e., implant 232) may include only one reservoir (i.e., reservoir 238). The reservoirs 38 of FIG. 1 can optionally hold different therapeutic agents 36 at the same time; stated another way, each reservoir 38 can hold a different therapeutic agent 36, or each reservoir 38 can hold at least two therapeutic agents 36. Thus, the implant according to the present invention is configured for delivering a plurality of therapeutic agents to the corporeal body via the reservoir and the plurality of channels; examples of such implants include implant 32 (FIG. 1) and implant 232 (FIG. 3). Further, implant 32 may be formed such that no seal or seal cap is formed over any of channels 40 prior to release of any therapeutic agent 36.

A corporeal body herein means the physical body of a human being or of an animal (i.e., a veterinary patient). Thus, a corporeal body is one of flesh and bones. The corporeal body can be alive or dead. The corporeal body can also be referred to as a patient body herein, which includes both human and veterinary "patients", alive or dead. Therapeutic agents can also be referred to herein as drugs or medicinal agents. Therapeutic agents can be formed, for example, as a liquid, a solid, a capsule, or a bead.

Further, FIG. 1 shows that implant 32 includes a body 44 implantable at the selected location. Body 44 defines reservoir 38 and channels 40 and includes an exterior surface 46. The reservoir of the present invention can be a cavity or an enclosed pocket (closed but for channels extending to the surface of the body of the implant) formed by the body of the implant. The reservoir can be formed by the core (i.e., the central interior portion) of the body, rather than in the exterior surface of the body. The reservoir can occupy a substantial portion of the core but yet still have elongate channels running from the reservoir to the exterior surface. Reservoir 38 is a cavity in body 44. Reservoir 38 is not a through-hole through body 44. Channels 40 fluidly communicate reservoir 38 with exterior surface 46 and thereby forms the pathways for the at least one therapeutic agent 36 to move from reservoir 38 to exterior surface 46. That is, channels 40 fluidly communicate reservoir 38 with exterior surface 46 and thereby convey at least one therapeutic agent 36 from reservoir 38 to exterior surface 46. FIG. 1 shows the body 44 of the implant 32 being the implant 32 itself.

Further, FIG. 1 shows that implant 32 is formed as a hip prosthesis and that corporeal body 34 is formed as a hip. More specifically, FIG. 1 shows a sectional view of a short-term femoral hip implant 32 (which is one type of orthopaedic implant) which forms part of the upper femur (or, thighbone) and is thus load-bearing. The body 44 of the femoral hip prosthesis 32 of FIG. 1 (the body 44 and the femoral hip prosthesis 32 being coextensive relative to one another and thus being the same structural member in FIG. 1) includes a stem (the downward extending portion of implant 32 in FIG. 1) which can be inserted into the upper femur of a body 34 and a femoral head (the ball portion of implant 32 in FIG. 1) which is received by and mates with an acetabulum (i.e., the patient's natural acetabulum, or a prosthetic acetabular cup). FIG. 1 shows that both the stem and the femoral head include reservoirs 38 and a plurality of channels 40 running from the respective reservoirs 38 to the exterior surface 46 of the implant 32. Depending upon the size of reservoir 38 relative to exterior surface 46 and/or the nearness of reservoir 38 to exterior surface 46, channels 40 can be formed as holes or apertures in body 44. In use, therapeutic agent 36 is inserted in reservoirs 38 prior to and/or after implantation of implant in body 34. Therapeutic agent 36 can then migrate into channels 40 and travel via channels 40 to exterior surface 46 (channels 40 forming holes in exterior surface 46). Therapeutic agent 36 exits channels 40 and contacts treatment site 42, which can be for example bone or tissue.

Figure 17:
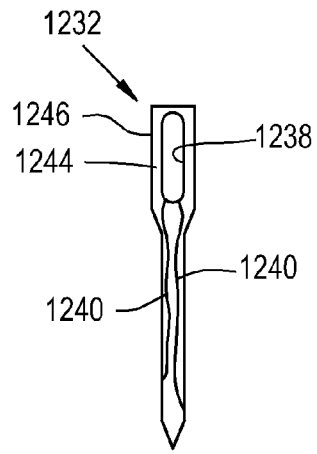
FIG. 17 is a schematic representation of a sectional view of an orthopaedic nail according to the present invention.
Figure 18:
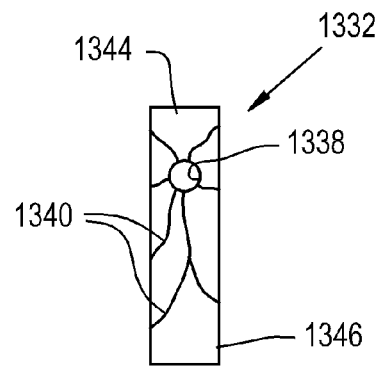
FIG. 18 is a schematic representation of a sectional view of an orthopaedic plate according to the present invention.
Figure 19:
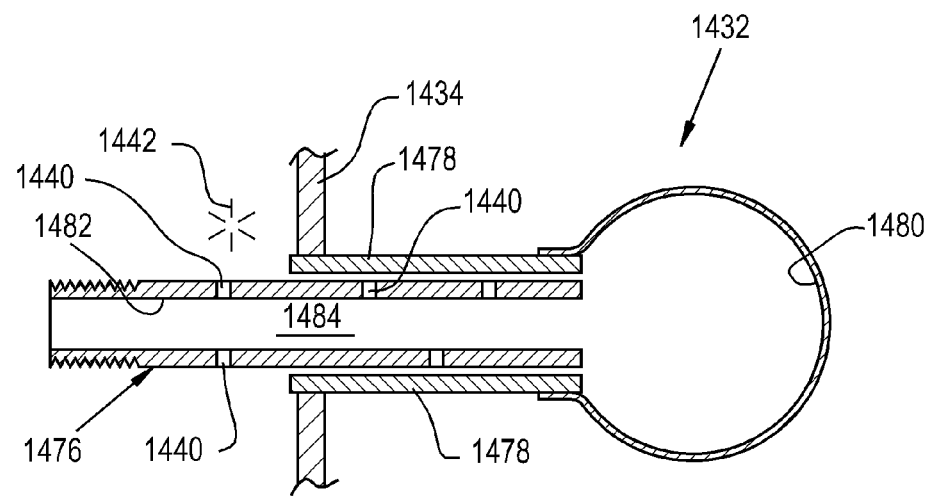
FIG. 19 is a schematic representation of a sectional view of an external fixation device according to the present invention.

The orthopaedic implant of the present invention can be a prosthesis, a nail, a plate, or an external fixation device formed as an implantable pin. FIGS. 1-16 and 20-27 shows orthopaedic implants which are prostheses. A prosthesis is an implant that substitutes for or supplements a missing or defective part of the corporeal body. FIG. 17 shows an orthopaedic implant which is a nail. FIG. 18 shows an orthopaedic implant which is a plate. FIG. 19 shows an orthopaedic implant which is an external fixation device with an implantable pin.

Figure 2:
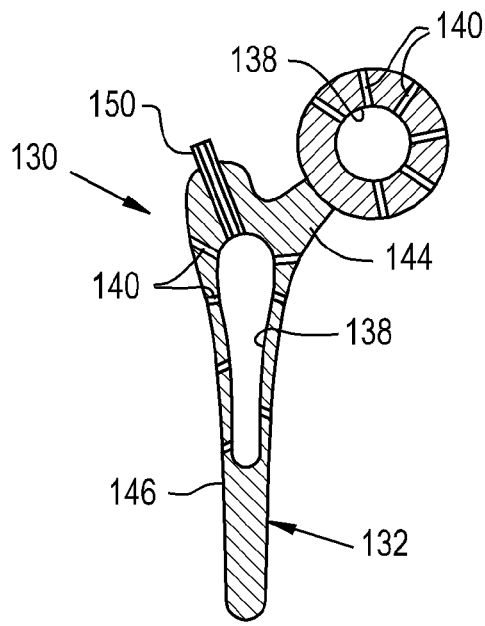
FIG. 2 is a schematic representation of a sectional view of a short-term femoral hip implant system according to the present invention.

FIG. 2 shows another embodiment of the orthopaedic implant according to the present invention. Structural features in FIG. 2 corresponding to similar features in FIG. 1 have reference characters raised by a multiple of 100. Short-term orthopaedic implant system 130 includes a short-term prosthetic implant 132 and an attachment feature 150. Body 144 defines reservoir 138 and channels 140 running from reservoir 138 to exterior surface 146. Attachment feature 150 is for attaching a port (not shown in FIG. 2) thereto. The attachment feature 150 can be a tubular element. The attachment feature 150 and the port can be used to refill the reservoir 138 with a therapeutic agent. Upon filling reservoir 138 with the therapeutic agent (either initially and/or as a refill) via attachment feature 150, the therapeutic agent can move from the reservoir 138 to the treatment site via channels 140.

FIG. 3 shows another embodiment of the orthopaedic implant according to the present invention. Structural features in FIG. 3 corresponding to similar features in prior figures have reference characters raised by a multiple of 100. FIG. 3 shows a sectional view of another short-term hip implant 232. Prosthetic implant 232 is formed as an acetabular cup, which receives a femoral head. The body 244 of the acetabular cup 232 is the acetabular cup 232 in FIG. 3. Body 244 defines reservoir 238 and a plurality of channels 240 running from reservoir 238 to exterior surface 246. Upon filling reservoir 238 with the therapeutic agent (either initially and/or as a refill), the therapeutic agent moves from the reservoir 238 to the treatment site via channels 240.

Figure 4:
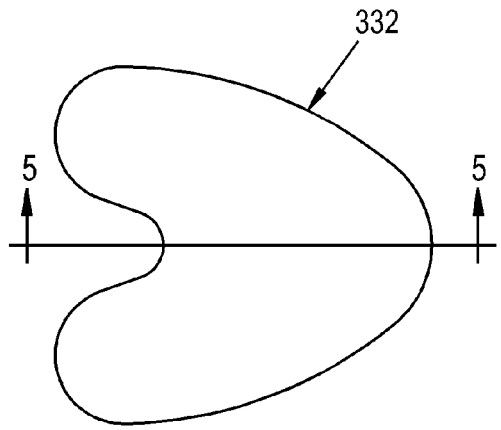
FIG. 4 is a schematic representation of a top view of a short-term femoral knee implant according to the present invention.
Figure 5:
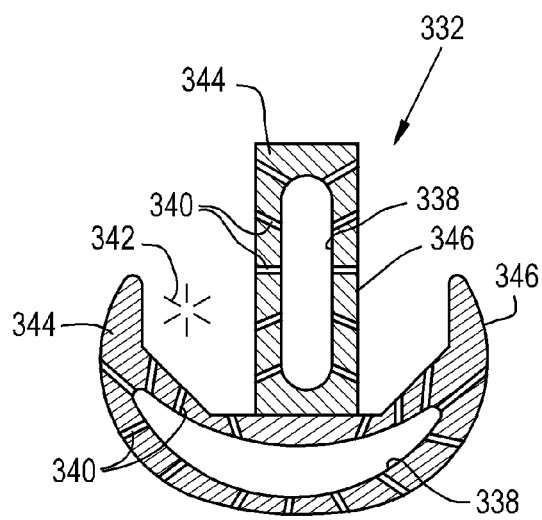
FIG. 5 is a schematic representation of a sectional view of the short-term femoral knee implant taken along line 5-5 in FIG. 4.
Figure 6:
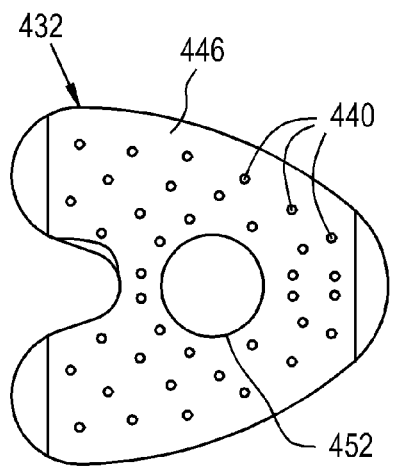
FIG. 6 is a schematic representation of a top view of a short-term femoral knee implant according to the present invention.
Figure 7:
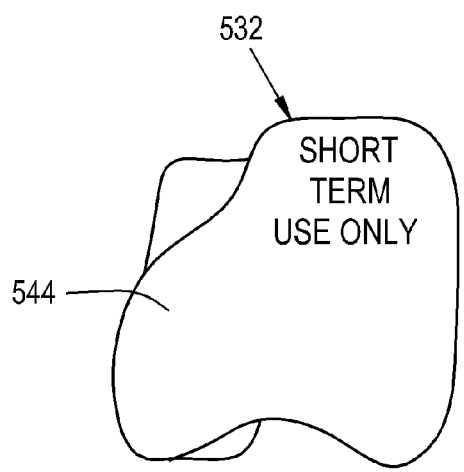
FIG. 7 is a schematic representation of a front view of short-term femoral knee implant.

FIGS. 4-8 show additional embodiments of orthopaedic implants according to the present invention. More specifically, FIGS. 4-8 show short-term orthopaedic implants formed as prosthetic knee implants, both femoral and tibial prosthetic knee implants. Structural features in FIGS. 4-7 corresponding to similar features in prior figures have reference characters raised by a multiple of 100. FIGS. 4 and 5 show that the body 344 of implant 332 is the femoral knee implant 332. Body 344 includes a lower portion (the generally U-shaped piece in FIG. 5) and an optional stem (the vertical, upstanding piece atop the lower portion in FIG. 5). Both the lower portion and the stem include drug reservoirs 338 and drug delivery channels/holes 340 communicating the respective reservoir 338 with exterior surface 346 to deliver the therapeutic agent(s) in the reservoirs 338 to the treatment site(s) 342. FIG. 6 shows a top view of femoral knee implant 432 similar to the implant 332 shown in FIG. 5. Channels 440 are shown as exit holes in exterior surface 446 of the lower portion. The circle in FIG. 6 represents an optional, upstanding stem 452. FIG. 7 shows a front view of short-term femoral knee implant 532 marked with lettering which is more radiopaque than the implant body 544 so that the letters are visible on an X-ray or fluoroscope, as shown in FIG. 7. Upon filling the reservoirs for FIGS. 5 and 6 with the therapeutic agent (either initially and/or as a refill), the therapeutic agent can move from these reservoirs to the treatment site via channels 340, 440.

Figure 8:
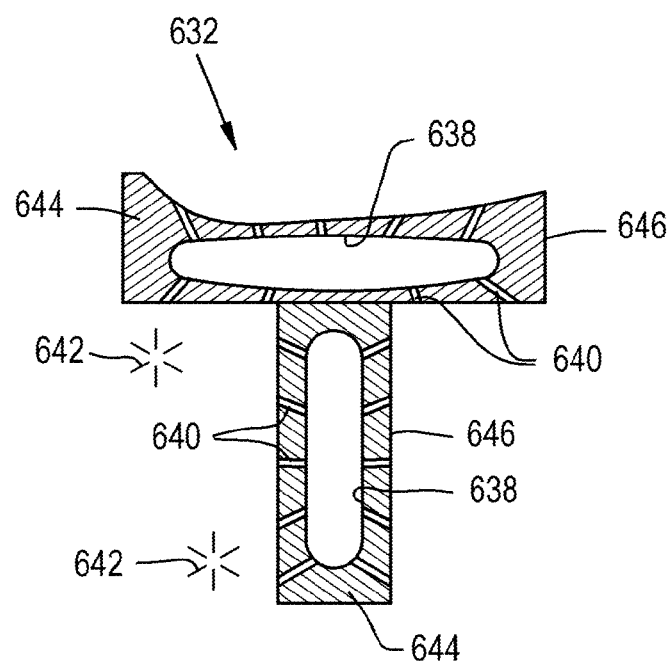
FIG. 8 is a schematic representation of a sectional view of a short-term tibial knee implant.

FIG. 8 shows a sectional view of a short-term tibial knee implant 632 according to the present invention. Structural features in FIG. 8 corresponding to similar features in prior figures have reference characters raised by a multiple of 100. The body 644 of implant 632 is the tibial knee implant 632. Body 644 includes a tibial tray (the generally horizontal piece in FIG. 8) and an optional stem (the generally vertical piece below the horizontal piece in FIG. 8). Both the lower portion and the stem define drug reservoirs 638 and drug delivery channels/holes 640 communicating the respective reservoir 638 with exterior surface 646 to deliver the therapeutic agent(s) to the treatment site(s) 642. Upon filling reservoir 638 with the therapeutic agent (either initially and/or as a refill), the therapeutic agent can move from the reservoir 638 to the treatment site 642 via channels 640.

The implants according to the present invention shown in FIGS. 1-8 are thus short-term implants that can be used, for example, to treat infections within a corporeal body. Such short-term or temporary implants allow for the delivery of therapeutic agents, such as antibiotics, directly to the bone of a corporeal body and to surrounding tissue.

A device such as a port could be used to allow for post-operative injections of antibiotics into the implant. (See FIG. 2). This would allow for the delivery of multiple antibiotics throughout treatment. Reservoirs and/or channels in the implant would allow the antibiotics from these injections to be delivered over a time-period from hours to weeks. (FIGS. 1-8). Injection intervals of approximately a week would likely be well-accepted clinically. The drugs could be delivered to all bone and soft tissue surrounding the implant or only to specific locations. Variations of this concept would allow for a range of joint mobility from no motion at the joint to the mobility typical of a permanent total joint. These short-term implants can be held in the bone with a loose press-fit or with antibiotic or standard bone cement. In the case of bone cement, cement restrictors would also be included in the technology to prevent cement from sealing over the drug delivery holes.

Antibiotic cements typically provide useful local antibiotic levels for a duration of less than one week. The treatment time is frequently six to eight weeks. However, beyond one week, the antibiotic cement implants provide no useful amount of antibiotics. The implant according to the present invention, by contrast, allows the delivery of the correct dose of antibiotics continuously for any length of time required. Through a feature such as a port attached to the implant of the present invention, the implant reservoir can be refilled as often as necessary to provide the proper drug dosing.

The implant of the present invention allows for any number of antibiotics to be used at any time during treatment. An initial antibiotic can be used at the time of surgery. If the cell cultures indicate that a different antibiotic or dose would be more effective, that change in treatment regimen can be made in accordance with the present invention.

A short-term femoral hip implant, as discussed above, can include a stem and a separate head or could be a one-piece construction. Multiple sizes of stem and head size could be accommodated. A separate acetabular component could be provided, as discussed above. The femoral head could mate with a short-term acetabular component or with the patient's acetabulum. (See FIGS. 1-3). According to the present invention, drugs can be delivered to the acetabulum through the head of the femoral component if an acetabular component is not used (See FIG. 1) or through the acetabular component if one is used (See FIG. 3).

A short term knee implant can include a one-piece tibial component (combining the two pieces of a standard total knee replacement) and a one- or two-piece femoral component (the two-piece design would combine the condyles and stem). The present invention provides multiple sizes of tibia components and of stem and condyles (either combined as one piece or separate). (See FIGS. 4-8). Similar components are provided for shoulder, elbow, and other joints, according to the present invention.

Since the implants of FIGS. 1-8 are designed for short-term use, the short-term implants of the present invention can include markings which are both visible on the implant surface by the naked eye and visible by X-ray, as indicated above. These markings would clearly indicate that the implants are intended for short-term use only. (See FIG. 7).

The present invention provides an orthopaedic implant system (whether short-term, long-term, or non-permanent implants) which provide for continuously delivering drugs to a point near the implant or to the entire region surrounding the implant for extended periods of time. The implants according to the present invention shown in FIGS. 9-16 are long-term implants. Such implants can be used, for example, as total hip, knee, shoulder, and elbow joints within a patient body. The long-term implants of the present invention have a basic similarity with the short-term implants described above. Thus, structural features in FIGS. 9-16 corresponding to similar features in prior figures have reference characters raised by multiples of 100. Thus, similar to the short-term implants described above, the present invention further provides a long-term implant which would allow drugs to be delivered directly to the bone and surrounding tissue (or to any specific location). A device such as a port could be used to allow for post-operative injections of drugs into the long-term implant. (See FIG. 14). This would allow for the delivery of any number of drugs throughout treatment and allow for the refilling of drugs to provide proper drug dosing throughout treatment. Reservoirs and/or channels in the long-term implant according to the present invention would allow the drugs from these injections to be delivered over a time period from hours to weeks. (See FIGS. 9-16). The drugs could be delivered to all bone and soft tissue surrounding the implant or only to specific locations.

Figure 9:
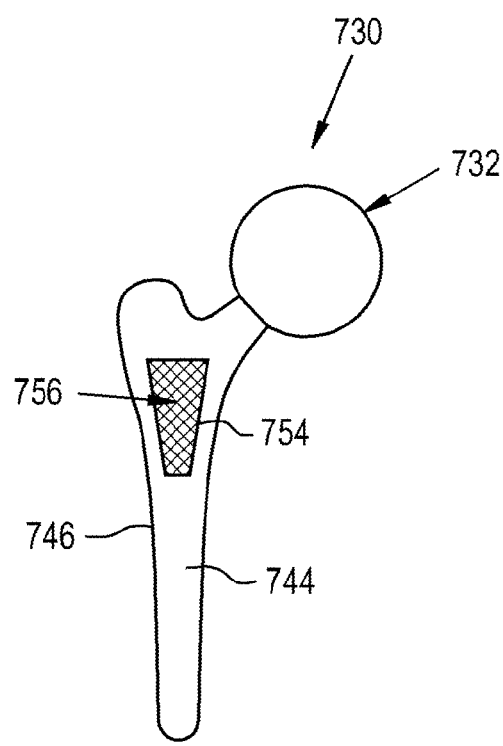
FIG. 9 is a schematic representation of a side view of a long-term femoral hip implant system according to the present invention.
Figure 10:
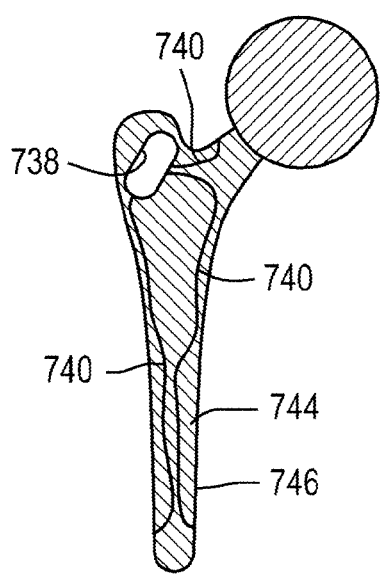
FIG. 10 is a schematic representation of a sectional view of the long-term femoral hip implant of FIG. 9.

FIGS. 9 and 10 show a long-term femoral hip prosthetic implant system 730 according to the present invention. Structural features in FIGS. 9 and 10 corresponding to similar features in prior figures have reference characters raised by multiples of 100. System 730 includes a long-term femoral hip prosthetic implant 732 and a porous surface 754 attached to the exterior surface 746. Similar to the short-term implants discussed above, implant has a body 744 defining a drug reservoir 738 and a plurality of drug delivery channels 740 running from the reservoir 738 to the exterior surface 746 so as to deliver a therapeutic agent(s) to a treatment site in the corporeal body. Porous surface 754 is configured for receiving bone and/or tissue ingrowth therein. Such ingrowth is shown by arrow 756 in FIG. 9. The porous surface 754 can be variously referred to as a porous member, a porous pad, or a scaffold. Drug delivery channels 740 can be routed by or through body 744 so as to avoid the ingrowth region. Stated another way, channels 740 can be routed by or through body 744 so as to avoid releasing therapeutic agents into porous surface 754. By contrast, channels 740 can be routed by or through body 744 so as to release drugs through the ingrowth porous surface 754. FIG. 9 shows channels 740 which avoid releasing drugs into porous surface 754. Upon filling reservoir 738 with the therapeutic agent (either initially and/or as a refill), the therapeutic agent can move from the reservoir 738 to the treatment site via channels 740.

Figure 11:
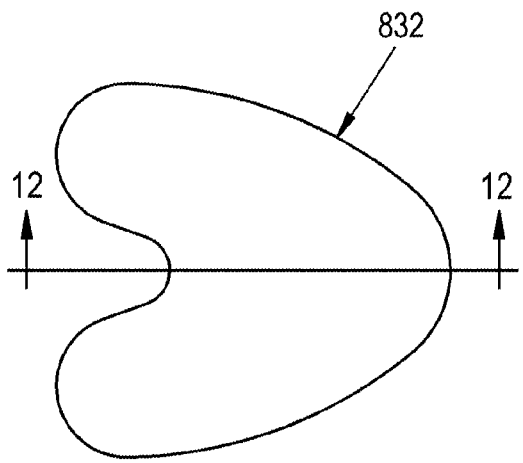
FIG. 11 is a schematic representation of a top view of a long-term femoral knee implant according to the present invention.
Figure 12:
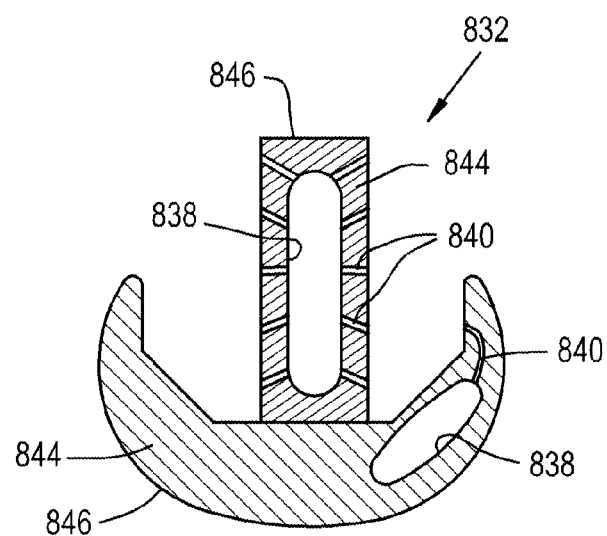
FIG. 12 is a schematic representation of a sectional view of the long-term femoral knee implant taken along line 12-12 in FIG. 11.

FIGS. 11 and 12 show a long-term femoral knee implant according to the present invention. Structural features in FIGS. 11 and 12 corresponding to similar features in prior figures have reference characters raised by multiples of 100. The body 844 of implant 832 is the femoral knee implant 832. Body 844 includes a lower portion (the generally U-shaped piece in FIG. 12) and an optional stem (the vertical, upstanding piece atop the lower portion in FIG. 12). Both the lower portion and the stem include drug reservoirs 838. The stem further includes drug delivery channels/holes 840 communicating the respective reservoir 838 with exterior surface 846 to deliver the therapeutic agent(s) to the treatment site(s) 846. The lower portion also includes at least one drug delivery channel 840 leading from reservoir to a treatment site. Upon filling reservoir 838 with the therapeutic agent (either initially and/or as a refill), the therapeutic agent can move from the reservoir 838 to the treatment site via channels 840.

Figure 13:
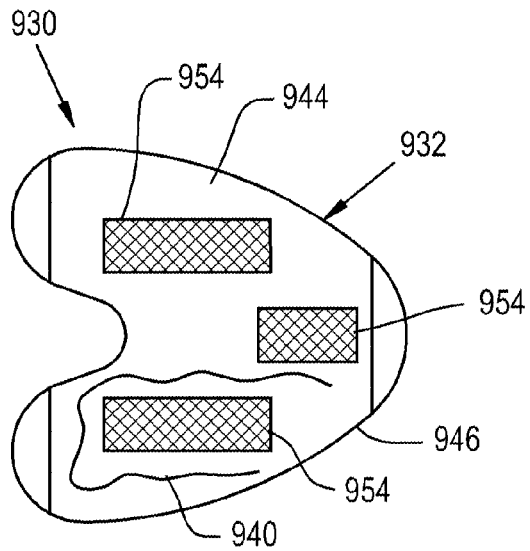
FIG. 13 is a schematic representation of a top view of a long-term femoral knee implant system according to the present invention.

FIG. 13 shows a long-term femoral knee implant system 930 according to the present invention. Structural features in FIG. 13 corresponding to similar features in prior figures have reference characters raised by multiples of 100. System 930 includes a prosthetic implant 932 similar to the implant 832 of FIG. 12 but with a plurality of ingrowth porous surfaces 954 attached to the body 944 of implant 932. Each porous surface 954 is configured for receiving bone and/or tissue ingrowth therein. Further, while the reservoir cannot be seen in FIG. 13, a drug delivery channel 940 leading from the drug reservoir is shown in FIG. 13. The reservoir of FIG. 13 can be situated just under exterior surface 946 as reservoir 838 is shown in FIG. 12. Channel 940 routes around (and thereby avoids) ingrowth pads 954. Upon filling the reservoir of implant 932 with the therapeutic agent (either initially and/or as a refill), the therapeutic agent can move from the reservoir of implant 932 to the treatment site via channels 940.

Figure 14:
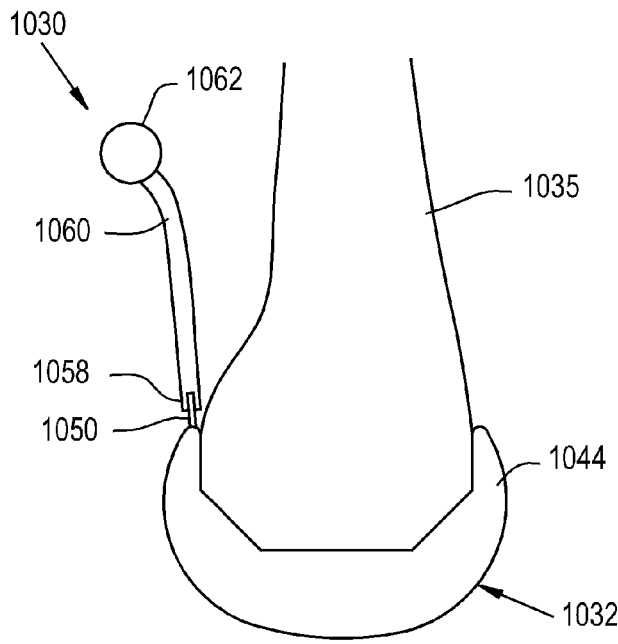
FIG. 14 is a schematic representation of a side view of a long-term femoral knee implant system according to the present invention, the long-term femoral implant being attached to a femur.

FIG. 14 shows a long-term femoral knee implant system 1030 according to the present invention. Structural features in FIG. 14 corresponding to similar features in prior figures have reference characters raised by multiples of 100. System 1030 includes a prosthetic implant 1032 similar to the implant 832 of FIG. 12. Implant 1032 is attached to a femur 1035. The system 1030 further includes an attachment feature or element 1050 (such as a tubular element) for an injection port 1058, an injection port 1058, a catheter 1060, and a reservoir 1062 remote to the implant 1032. The injection port is provided for additional refilling of drugs into the implant 1032, which includes at least one channel for routing the therapeutic agent to the treatment site. Since an external reservoir 1062 is attached to implant 1032, implant body 1044 may or may not define an additional internal reservoir. Upon filling the internal reservoir of implant 1032 with the therapeutic agent (either initially and/or as a refill) via attachment element 1050, injection port 1058, catheter 1060, and external reservoir 1062, the therapeutic agent can move from the reservoir of implant 1032 to the treatment site via the drug delivery channels. If implant 1032 does not have an internal reservoir, then the therapeutic agent moves to the treatment site via the drug delivery channels from external reservoir 1062 via catheter 1060, injection port 1058, and attachment element 1050.

Figure 15:
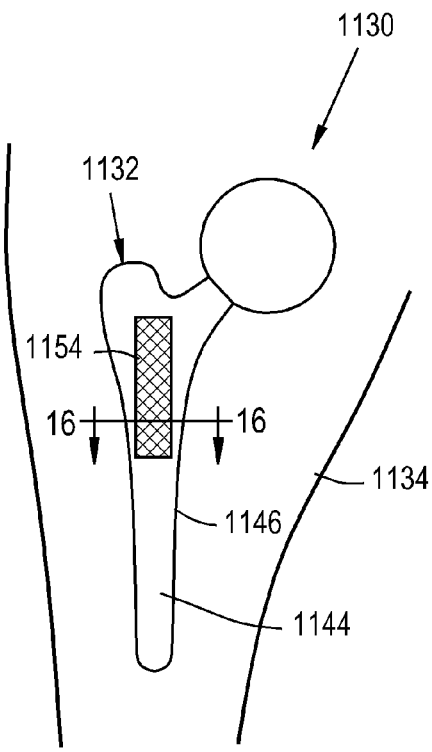
FIG. 15 is a schematic representation of a side view of a long-term femoral hip implant system according to the present invention.
Figure 16:
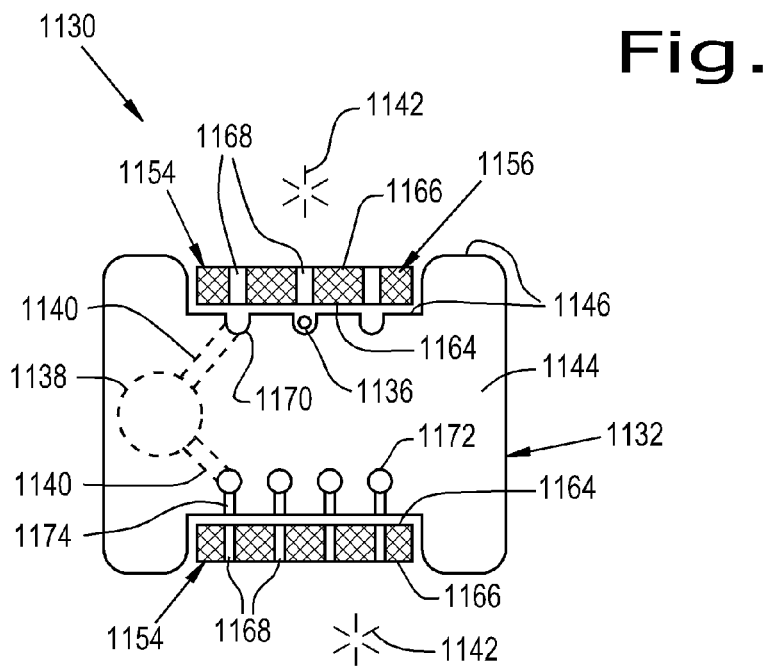
FIG. 16 is a schematic representation of a sectional view of the long-term femoral hip implant system of FIG. 15 taken along line 16-16.

FIGS. 15 and 16 show a long-term femoral hip implant system 1130 according to the present invention. Structural features in FIGS. 15 and 16 corresponding to similar features in prior figures have reference characters raised by multiples of 100. FIG. 15 shows long-term femoral hip implant system 1130 including a long-term femoral hip prosthetic implant 1132 and an ingrowth porous surface 1154. FIG. 16 shows a first porous surface 1154 on the top (as oriented in FIG. 16) of the implant body 1144 or substrate 1144 (in each of the figures, the body 1144 can also be referred to as a substrate) and a second porous surface 1154 on the bottom (as oriented in FIG. 16) of the body 1144. Porous surfaces 1154 are configured for receiving bone and/or tissue ingrowth therein, as shown by arrow 1156. While FIG. 16 shows some space between porous surfaces 1154 and body 1144, it is understood that this space is for illustrative purposes and that porous surfaces 1154 can be flush with body 1144 but for any adhesive that may be used to attach surfaces 1154 with exterior surface 1146 of body 1144. Each porous surface 1154 includes a first side 1164 attached to exterior surface 1146 of body 1144 and a second side 1166 opposing said first side 1164. Each porous surface 1154 includes a through-hole 1168 running from first side 1164 to second side 1166. Through-hole 1168 is configured for communicating the therapeutic agent 1136 from first side 1164 to second side 1166 and thereby for communicating the therapeutic agent 1136 to the treatment site 1142. The through-holes 1168 in porous surfaces 1154 lead to surface channels 1170 and sub-surface channels 1172, respectively. Channels 1170 and 1172 can function essentially the same as channels 40 in that they are drug delivery channels. FIG. 16 shows a reservoir 1138 and connecting channels 1140 in broken lines; for, it is understood that such a reservoir 1138 and connecting channels 1140 (connecting reservoir 1138 with channels 1170 and/or 1172) may not be visible in this section, or, alternatively, that such a reservoir 1138 and connecting channels 1140 can be optional (stated another way, the implant 1132 would not contain such an interior reservoir 1138 and connecting channels 1140 leading from the reservoir 1138 to the surface channels 1170 or the sub-surface channels 1172).

Further, FIG. 16 shows that exterior surface 1146 of body 1144 can define a surface channel 1170 which is in communication with and cooperates with channel 1140 and through-hole 1168 of porous surface 1154 to provide the therapeutic agent 1136 from the reservoir 1138 to the treatment site 1142. FIG. 16 shows a plurality of such surface channels 1170, each of which can optionally be connected to reservoir 1138 via a respective connecting channel 1140, as discussed above. If implant 1132 has reservoir 1138 and connecting channels 1140, then upon filling reservoir 1138 with the therapeutic agent (either initially or as a refill), the therapeutic agent can move from reservoir 1138 to the treatment site via the channels 1140 and 1170. If implant 1132 does not have reservoir 1138 and connecting channels 1140, then surface channels 1170 can be filled with the therapeutic agent (either initially and/or as a refill) and the therapeutic agent moves via surface channels 1170, through through-holes 1168, to the treatment site 1142. The therapeutic agent can also be provided to the bone and/or tissue growing into porous surface 1154.

Further, FIG. 16 shows that channels 1140 running from reservoir 1138 can connect to the sub-surface channels 1172. Sub-surface channels 1172 and through-holes 1168 in porous surface 1154 are aligned with and cooperate with one another to provide the therapeutic agent 1136 from the reservoir 1138 to the treatment site 1142. Holes 1174 (which can also be considered as channels of the present invention, like channels 40) are also provided in body 1144 leading from subsurface channels 1172 to exterior surface 1146. These holes 1174 can be considered to be part of the respective channels 1140 and 1172.

FIGS. 15 and 16 thus also show an orthopaedic implant system 1130 including an orthopaedic implant 1132 and a porous surface 1154. The orthopaedic implant 1132 includes a body 1144 implantable at a selected location within a corporeal body 1134 and configured for delivering a therapeutic agent 1136 to corporeal body 1134. Body 1144 of implant 1132 includes an exterior surface 1146 defining a plurality of surface channels 1170 and, as discussed above, can have an absence of a therapeutic agent reservoir 1138. The broken lines of the reservoir 1138 in FIG. 16, as stated above, indicates that the reservoir 1138 is optional. The plurality of surface channels 1170 are configured for receiving, holding, delivering, and being refilled with the therapeutic agent 1136 after implant 1132 has been implanted in corporeal body 1134. Orthopaedic implant 1132 is a prosthesis. Alternatively, implant 1132 can be formed as a nail (FIG. 17), a plate (FIG. 18), or an external fixation device with an implantable pin (FIG. 19). Porous surface 1154 is attached to exterior surface 1146. Porous surface 1154 is configured for receiving at least one of bone and tissue ingrowth therein, as shown by arrow 1156. As discussed above, porous surface 1154 includes a first side 1164 attached to exterior surface 1146 and a second side 1166 opposing first side 1164. Porous surface 1154 includes a plurality of through-holes 1168 running from first side 1164 to second side 1166. The plurality of surface channels 1170 communicate and cooperate with the plurality of through-holes 1168 to provide the therapeutic agent 1136 from the plurality of surface channels 1170, then to first side 1164 of porous surface 1154, and then to second side 1166 of porous surface 1154. Surface channels 1170 can be filled with the therapeutic agent (either initially and/or as a refill) and the therapeutic agent 1136 moves via surface channels 1170, through through-holes 1168, to the treatment site 1142.

Thus, the present invention could be applied to long-term implants with any type of porous coating or surface or to cemented implants. Drugs could be delivered through the porous coatings or be routed to regions without porous coatings (as disclosed above), depending on the requirements. (See FIGS. 9, 10, 13, 15, and 16). For delivery through the porous coatings, channels can be created on the surface of the implant substrate (the solid material of the implant to which the porous surface is attached—see FIG. 14) or below the surface, as disclosed above relative to FIGS. 15 and 16. For surface channels, holes can be drilled through the porous surface to the surface channels to create a path through which the drugs can be delivered. For sub-surface channels, holes must be drilled from the surface of the substrate (the body of the implant) to the sub-surface channels to create paths for drugs to be delivered. (See FIG. 16). This drilling can occur prior to attaching the porous coating/surface or after the porous coating/surface is attached. If this drilling occurs after the porous coating/surface is attached, the holes will be created through the porous coating/surface and the substrate/body surface. (See FIG. 16).

Cement restrictors can also be used according to the present invention to prevent cement from sealing over the drug delivery holes. The present invention can be applied to all types of total joint implants, such as total hip components, total knee components, total shoulder components, and total elbow components.

With regard to enhancing bone ingrowth and combating resorbtion, bone growth stimulators can be injected intraoperatively or postoperatively to enhance or speed bone ingrowth into porous material (i.e., porous coatings or pads or surfaces on total joint components, on fusion devices (i.e., spinal fusion devices), or on bone augmentation components (i.e., tibial wedges)). These drugs could also be injected months to years post-operatively, using a long-term implant according to the present invention, to combat bone resorbtion due to such causes as stress-shielding, osteolysis, or bone metabolic disorders.

With regard to oncology, the implant of the present invention would similarly allow for delivery of drugs to some or all tissue surrounding the implant. The implants of the present invention may be cemented. The present invention provides a way to route the drugs around the regions of cement and provides a way for preventing the cement from sealing over the drug delivery holes.

The implants according to the present invention shown in FIGS. 17-19 are non-permanent implants. Such implants can be trauma products, such as nails, plates, and external fixation devices. The non-permanent implants of the present invention are not necessarily limited to these devices. The non-permanent implants of the present invention have a basic similarity with the short-term and long-term implants described above. Thus, structural features in FIGS. 17-19 corresponding to similar features in FIG. 1 have reference characters raised by multiples of 100. Thus, similar to the short-term and long-term implants described above, the present invention further provides a non-permanent implant which would allow drugs to be delivered directly to the bone and surrounding tissue (or to any specific location). Reservoirs and/or channels in the non-permanent implant according to the present invention would allow the drugs to be delivered to the treatment site and could be refilled. A nail according to the present invention is shown in FIG. 17. A plate according to the present invention is shown in FIG. 18. An external fixation device according to the present invention is shown in 19.

Nails are temporary, intramedullary devices. They are typically used to treat traumatic fracture. The risk of infection can be high especially in the case of open fractures. The present invention would allow antibiotics to be delivered to the bone surrounding the nail as a preventative or to treat an infection if one develops.

With regard to bone growth, in the case of fractures, there are instances in which the delivery of bone growth stimulators directly to the region of the fracture(s) would be beneficial. This is especially true in difficult cases such as non-unions, bony defects, and osteotomies. The nail according to the present invention would allow for such delivery bone growth stimulators directly to the region of the fracture(s).

With regard to oncology, nails can be used to treat fractures associated with bone tumors. They can also be used to help prevent a fracture where cancer has weakened bone. The nail according to the present invention provides for localized delivery of oncological drugs in the region of tumors which may improve results in slowing/halting tumor growth. This ability for localized delivery provided by the nail according to the present invention may also lessen the need/dose of systemic drugs, resulting in fewer side effects.

FIG. 17 shows an orthopaedic nail 1232 implantable in the corporeal body. Structural features in FIG. 17 corresponding to similar features in prior figures have reference characters raised by multiples of 100. Nail 1232 includes a body 1244 defining a reservoir 1238 and a drug delivery channel 1240 leading from drug reservoir 1238 to exterior surface 1246 of nail 1232. The present invention thus provides an orthopaedic nail 1232 with a drug delivery portion, which is similar to that, for instance, for long-term implants, such as a femoral hip implant (such as a hip stem). This design allows drugs to be delivered directly to all areas of the bone or to any specific location. (FIG. 17). A device such as a port could be used to allow for post-operative injections of drugs into the nail 1232. This would allow for the delivery of any number of drugs throughout treatment. Reservoirs 1238 and/or channels 1240 in the nail 1232 would allow the drugs from these injections to be delivered over a time period from hours to weeks. Thus, upon filling reservoir 1238 with the therapeutic agent (either initially and/or as a refill), the therapeutic agent can move from the reservoir 1238 to the treatment site via channels 1240. The drugs could be delivered to all bone tissue surrounding the implant or only to specific locations. All types of nails could utilize this technology, including antegrade and retrograde versions of femoral, tibial, and humeral nails.

Orthopaedic plates treat many of the same indications as nails; however, plates are applied to the outside of the bone. Plates offer the same opportunities for delivering drugs locally. Since nails are intramedullary, they can be used to deliver drugs, according to the present invention, primarily to the bone tissue. Since plates are applied to the outside of the bone, they can be used to deliver drugs, according to the present invention, to both bone and soft tissues. Examples of potential soft tissue treatments benefited by localized drug delivery include the enhancement of soft tissue ingrowth or healing, the prevention of infection by the delivery of antibiotics, and the treatment of nearby soft tissue tumors with localized delivery of oncological drugs.

FIG. 18 shows an orthopaedic plate 1332 that is implantable in a corporeal body. Structural features in FIG. 18 corresponding to similar features in prior figures have reference characters raised by multiples of 100. Plate 1332 includes a body 1344 defining a reservoir 1338 and a drug delivery channel 1340 leading from drug reservoir 1338 to exterior surface 1346 of plate 1332. Upon filling reservoir 1338 with the therapeutic agent (either initially and/or as a refill), the therapeutic agent can move from the reservoir 1338 to the treatment site via channels 1340.

Thus, the drug delivery portion of plate is similar to that for orthopaedic nails according to the present invention. Plate allows drugs to be delivered directly to the bone and surrounding tissue (or to any specific location). A device such as a port could be used to allow for post-operative injections of drugs into plate. This would allow for the delivery any number of drugs throughout treatment. Reservoirs 1338 and/or channels 1340 in the plate implant 1332 allow the drugs from these injections to be delivered over a time-period from hours to weeks. The drugs could be delivered to all bone and soft tissue surrounding the plate implant 1332 or only to specific locations.

External fixation devices are temporary implants that are used to stabilize a fracture. These external fixation devices can be used for days to months. External fixation devices typically include several pins fixed in the bone and extending through the skin to a rigid plate, ring, rod, or similar stabilizing device. These devices carry the added risk of infection considering that the pins extend through the skin. Bacteria can travel along the pins directly to the soft tissue and bone. The present invention can be applied to external fixation devices. Thus, antibiotics or other anti-infective agents can be provided to the bone and soft tissue surrounding the pins. (FIG. 19). An external reservoir could be used to supply/pump antibiotics to the bone and soft tissue.

FIG. 19, for instance, shows an external fixation device 1432 according to the present invention which is a trauma device. Structural features in FIG. 19 corresponding to similar features in prior figures have reference characters raised by multiples of 100. External fixation device 1432 includes an implantable pin 1476, a sheath 1478 coupled with pin 1476, and a reservoir 1480 coupled with sheath 1478, pin 1476 defining a plurality of channels 1440. More specifically, pin 1476 includes a wall 1482 defining an inner spatial area 1484 and a plurality of drug delivery channels 1440 or holes 1440. Connected to the outer circumference of the pin 1476 is sheath 1478, which can be coaxial with pin 1476. Sheath 1478 serves to prevent drugs from exiting that portion of the external fixation device 1432 which is outside of the skin 1434. To the right (as oriented on the page of FIG. 19) of the wall of skin 1434 is space that is external to the corporeal body. Further, drug reservoir 1480 is attached to sheath 1478. Drug reservoir 1480 is shaped to allow attachment of the external fixation device 1432 to external fixation rods and/or plates (not shown). The therapeutic agent moves from drug reservoir 1480 to the inner spatial area 1484 of pin 1476, through channels/holes 1440 in pin wall 1482, and to the treatment site. Thus, upon filling reservoir 1480 with the therapeutic agent (either initially and/or as a refill), the therapeutic agent can move from the reservoir 1480 to the treatment site 1442 via inner spatial area 1484 and channel(s) 1440.

Figure 20:
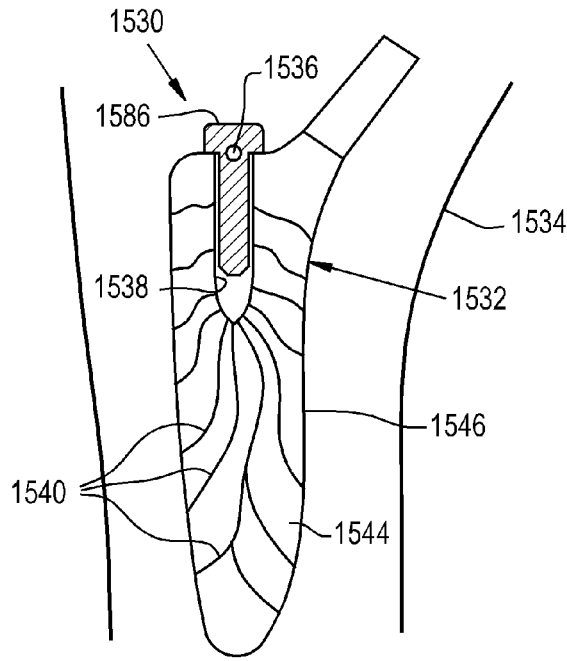
FIG. 20 is a schematic representation of a sectional view of an orthopaedic implant system including a therapeutic agent cartridge.
Figure 21:
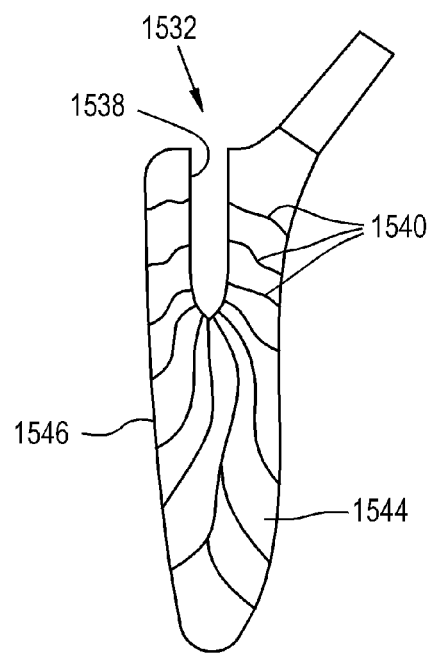
FIG. 21 is a schematic representation of a sectional view of an orthopaedic implant of FIG. 20 without the therapeutic agent cartridge inserted therein.

Shortcomings of temporary bone cement implants used to treat infections are discussed above. An additional shortcoming includes the difficulty of delivering adequate quantities of therapeutic agents through such implants to bone due to lack of blood flow. FIGS. 20-27 provide orthopaedic drug delivery implants which address this shortcoming. More specifically, FIGS. 20-21 provide therapeutic agent delivery via a removable and replaceable cartridge. Further, FIGS. 22-26 provide therapeutic agent delivery via leaching through an implant that is partially or totally porous. Further, FIG. 27 provides a modified reservoir design. The designs shown in FIGS. 20-27 can be used in short-term, long-term, or non-permanent orthopaedic implants. Structural features in FIGS. 20-27 corresponding to similar features in prior figures have reference characters raised by multiples of 100.

FIGS. 20 and 21 show an orthopaedic implant system 1530 including an orthopaedic implant 1532 and a cartridge 1586. More specifically, FIG. 20 shows cartridge 1586 inserted in implant 1532. FIG. 21, however, shows implant 1532 with cartridge 1586 removed. Implant 1532 is formed as, for example, a short-term femoral hip prosthetic implant 1532. Implant 1532 is implanted in corporeal body 1534. Implant 1532 is defined by its body 1544. Body 1544 defines a reservoir 1538 and a plurality of channels 1540 running from the reservoir 1538 to the exterior surface 1546 of body 1544. Cartridge 1586 is inserted into and thus received by reservoir 1538, which serves as a housing for cartridge 1586. Thus, reservoir 1538, as a housing for cartridge 1586, may be shaped to matingly accommodate and connect to cartridge 1586. Reservoir 1538 can be generally cup-shaped and thus be open to exterior surface 1546 (and thus reservoir 1538 can essentially be a blind hole in exterior surface 1546) so as to receive cartridge 1586. Cartridge 1586 contains at least one therapeutic agent 1536, which is shown in broken lines in FIG. 20. Cartridge 1586 is configured for releasing the therapeutic agent 1536 (shown as a circle in cartridge 1586) into reservoir 1538 and/or at least one channel 1540 such that the therapeutic agent 1536 moves away from reservoir 1538 in at least one channel 1540 and thus to exterior surface 1546 of body 1544. Cartridge 1586 is removable from reservoir 1538 and is replaceable with another cartridge 1586 after implant 1532 has been implanted in the corporeal body. The first cartridge 1586 is replaced when it is empty of the therapeutic agent (or when it has otherwise released the desired amount of therapeutic agent from the first cartridge 1586). The second cartridge 1586, which replaces the empty first cartridge 1586, is full (or has the desired amount of therapeutic agent therein) of therapeutic agent when it is inserted into reservoir 1538 and thereby replaces first cartridge 1586. Thus, the refilling of reservoir 1538 in system 1530 occurs by replacing first cartridge 1586 with a second cartridge 1586.

Thus, system 1530 can have implant body 1544 and a replaceable portion or cartridge 1586. (FIGS. 20-21). Replaceable cartridge 1586, as stated, contains therapeutics. Upon implantation, the surgeon can decide with what therapeutics to fill cartridge 1586. Over time, cartridge 1586 can be replaced with a new cartridge 1586 filled with the same therapeutic as before or a different therapeutic. Ideally, cartridge replacement would occur as a minor outpatient procedure.

The replaceable cartridge may be optionally formed relative to the implant. As a first option, the cartridge may be considered a distinct device relative to the implant but which can be directly attached to the implant, as shown in FIG. 20. As a second option, the cartridge may be considered a portion of the implant which can be detached from the implant body. As a third option, the cartridge may be a second replaceable implant located within the patient body away from the first implant (i.e., the femoral hip implant) but connected to the first implant, such as via a catheter. As a fourth option, the cartridge may be a device that is situated external to the patient body, while the implant (i.e., the femoral hip implant) is implanted in the patient body.

Figure 22:
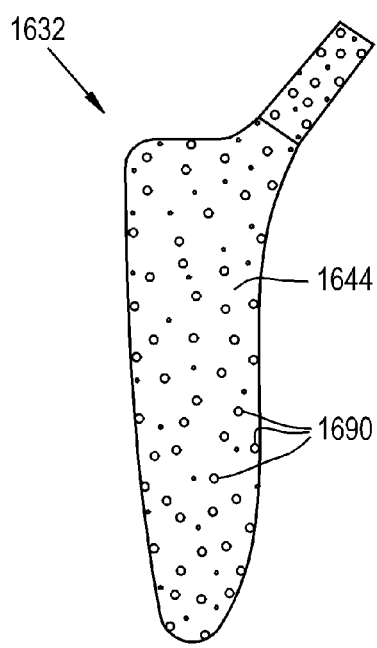
FIG. 22 is a schematic representation of a side view of an orthopaedic implant that is entirely porous.
Figure 23:
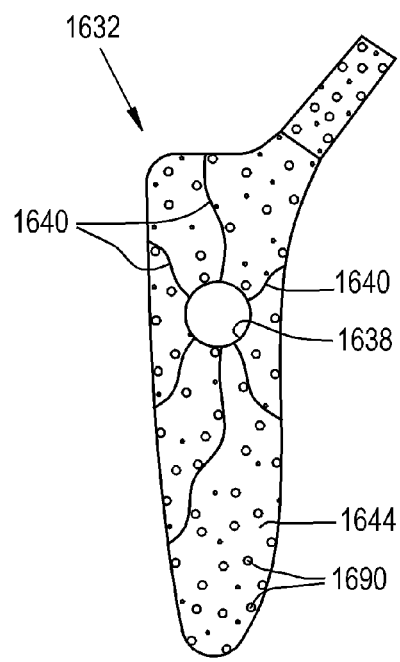
FIG. 23 is a schematic representation of a side view of an orthopaedic implant that is entirely porous and includes a reservoir and drug delivery channels according to the present invention.
Figure 24:
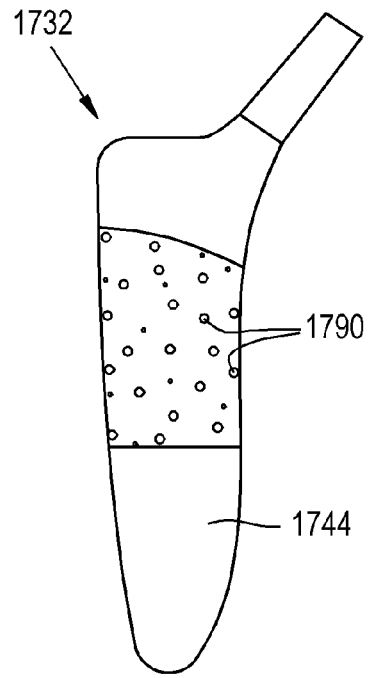
FIG. 24 is a schematic representation of a sectional view of an orthopaedic implant that is partially porous.
Figure 25:
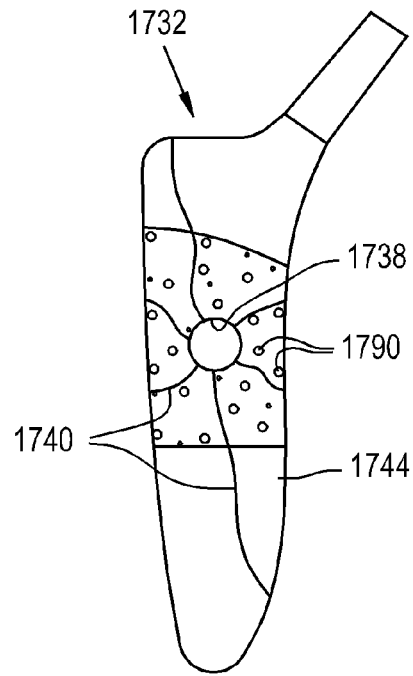
FIG. 25 is a schematic representation of a sectional view of an orthopaedic implant that is partially porous and includes a reservoir and drug delivery channels according to the present invention.
Figure 26:
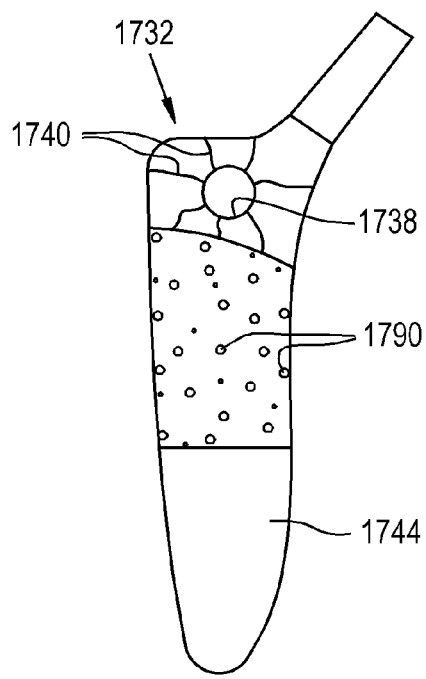
FIG. 26 is a schematic representation of a sectional view of an orthopaedic implant that is partially porous and includes a reservoir and drug delivery channels according to the present invention.
Figure 27:
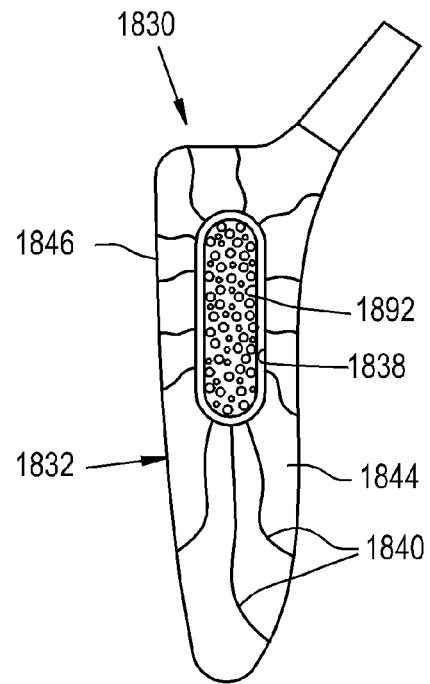
FIG. 27 is a schematic representation of a sectional view of an orthopaedic implant system according to the present invention including a sponge-like material.

FIGS. 22-26 show implants that are partially or totally porous to facilitate therapeutic agent delivery via leaching through the respective implant. In much the same manner of powder metallurgy bearings that are self-lubricating, therapeutic agents may be delivered to the patient body from an implant that is partially or totally porous. (FIGS. 22-26). Therapeutics will leach from the porous portions of the implant to the body. Such implants may also contain drug delivery channels, reservoirs, and the various ways of recharging therapeutics as previously discussed herein. FIGS. 22 and 23 each shows a femoral hip prosthetic implant 1632 in which the entire body 1644 of the implant 1632 is porous to facilitate leaching of therapeutic agents therefrom. Pores are labeled as 1690. The implant 1632 of FIG. 22, however, does not include in addition thereto a drug reservoir or drug delivery channels. Thus, the therapeutic agent is delivered via the pores 1690 of implant 1632 to the treatment site, which can be within or outside of the pores 1690. By contrast, FIG. 23 shows a drug reservoir 1638 and drug delivery channels 1640 embedded in or defined by the body 1644 of the implant 1632. Thus, upon filling reservoir 1638 with the therapeutic agent (either initially and/or as a refill), the therapeutic agent can move from the reservoir 1638 to the treatment site via channels 1640. FIGS. 24-26 each shows a femoral hip prosthetic implant 1732 in which a portion of the body 1744 of the implant 1732 is porous to facilitate leaching of therapeutic agents therefrom. The porous portion of body 1744 is labeled as 1790. The implant 1732 of FIG. 24, however, does not include in addition thereto a drug reservoir or drug delivery channels. Thus, the therapeutic agent can be delivered via the porous portion 1790 to the treatment site, which can be within or outside of the porous portion 1790. By contrast, the implants 1732 of FIGS. 25 and 26 do include in addition thereto a drug reservoir 1738 and drug delivery channels 1740. FIG. 25 shows the reservoir 1738 embedded in or defined by the porous portion 1790 of the body 1744 of the implant 1732 and drug delivery channels 1740 at least partially embedded in or defined by the porous portion 1790 of the body 1744 of the implant 1732. Thus, upon filling reservoir 1738 with the therapeutic agent (either initially and/or as a refill), the therapeutic agent can move from the reservoir 1738 to the treatment site (which can be either within or outside of the porous portion 1790) via channels 1740. FIG. 26 shows that the reservoir 1738 is not located in the porous portion 1790 and shows the drug delivery channels 1740 at least in part leading to the porous portion 1790. Thus, upon filling reservoir 1738 with the therapeutic agent (either initially and/or as a refill), the therapeutic agent can move from the reservoir 1738 to the treatment site (which can be either within or outside of the porous portion 1790) via channels 1740.

FIG. 27 shows an orthopaedic implant system 1830 with a femoral hip prosthetic implant 1832 and a sponge-like or spongy material or element 1892. Similar to the implants discussed above, the body 1844 of the implant 1832 defines a drug reservoir 1838 and drug delivery channels 1840 leading from the reservoir 1838 to the exterior surface 1846 of the body 1844. The reservoir 1838 contains or houses the spongy element 1892. The purpose of this material is to control dispersion of the therapeutic agents from the reservoir 1838 into the drug delivery channels 1840, to keep bone and tissue from growing into and filling the reservoir 1838, and/or to stiffen the implant 1832. Upon filling reservoir 1838 with the therapeutic agent (either initially and/or as a refill) and having positioned sponge-like material 1892 in reservoir 1838, the therapeutic agent can move from the reservoir 1838 (and thus also from spongy element 1892) to the treatment site via channels 1840. Depending upon the outcome desired, the material of the sponge-like element 1892 can be a number of possibilities. For example, if the sponge 1892 is to remain in reservoir 1838 for a long time, then a Polyvinyl Alcohol (PVA) or Ivalon sponge, for example, can be used. On the other hand, if the sponge 1892 is to last a shorter amount of time, then a collagen based material (i.e., Instat, by Johnson and Johnson, for example) or a gelatin sponge (i.e., Gelfoam, by Pfizer, for example), for example, can be used. These examples of the sponge 1892 are provided by way of example, and not by way of limitation.

Any of the devices according to the present invention described above can include a single or multiple attachment features (such as connections for catheters or ports) and a single or multiple sets of reservoirs and/or channels. The same therapeutic agent can be used in all reservoirs/channels, or several therapeutic agents can be used at one time. Separate reservoirs/channels allow each of the therapeutic agents to be delivered to a specific location on the implant, if desired.

Any of the internal (implanted) devices according to the present invention described above can include an internal reservoir (contained within the implant) in conjunction with delivery channels/paths to allow for short- and/or long-term delivery of the therapeutic agents. If an internal reservoir does not exist, the implant can contain delivery channels/paths to allow for the dispersion of the therapeutic agent.

Figure 28:
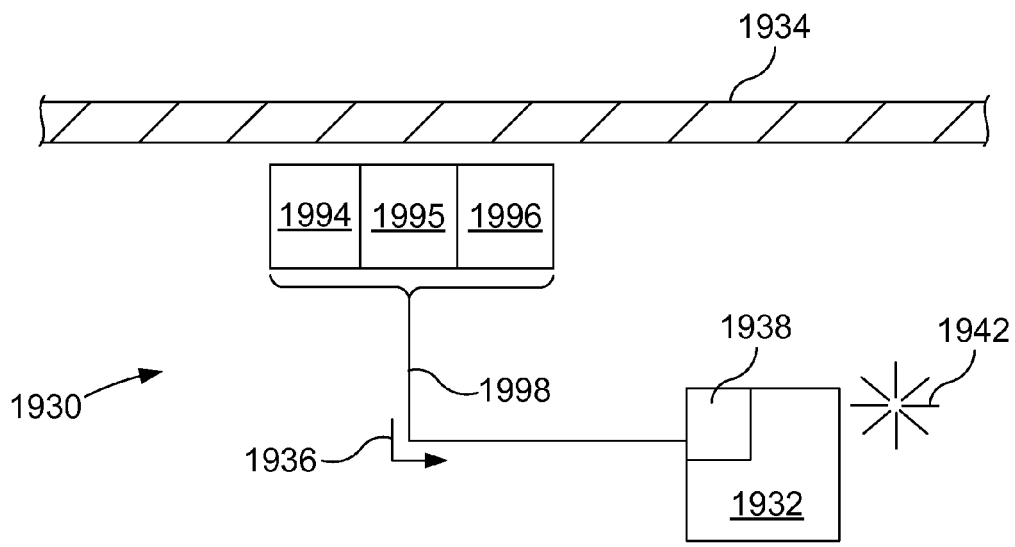
FIG. 28 is a schematic representation of an orthopaedic implant system according to the present invention.
Figure 29:
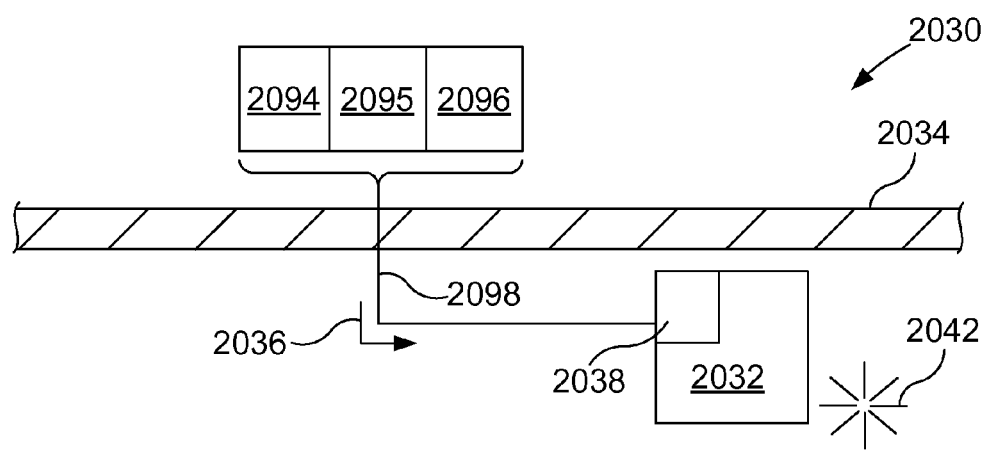
FIG. 29 is a schematic representation of an orthopaedic implant system according to the present invention.

According to the present invention, therapeutic agents can be introduced into the delivery channels/paths and/or implant reservoir of the implant of the present invention by one or more of the following ways:

a. Direct interface between a delivery vessel (such as a hypodermic syringe).

b. Direct attachment of a drug pump, external reservoir (external to the implant, but can be located internally or externally to the patient), and/or port to the implant; that is, a drug pump, external reservoir, and/or port can be attached directly to the implant. A catheter can be, but is not necessarily, located between the drug pump, external reservoir, and/or port and the implant. The therapeutic agent is then introduced into one of these intermediary devices by, for example, a hypodermic syringe. The therapeutic agent is then transferred to the implant delivery channels/paths and/or implant reservoir.

c. A drug pump, reservoir, and/or port can be implanted in the body in another location remote to the implant and/or can be connected to the implant by, for example, a delivery tube or catheter. FIG. 28 shows schematically this option for an orthopaedic implant system. According to system 1930, a reservoir 1994, a pump 1995, and a port 1996 are implanted under the skin of a patient body 1934 remote from implant 1932 and are shown connected via an implanted catheter 1998 to the reservoir 1938 of the implant 1932. The reservoir 1994, pump 1995, and port 1996 are thereby configured for delivering the therapeutic agent (shown by arrow 1936, which also shows the direction of travel of the therapeutic agent) from the reservoir 1994 to the treatment site 1942 via the implant 1932. Stated another way, the pump 1995 and port 1996 can cooperate with the reservoir 1938 to deliver the therapeutic agent 1936 via the catheter 1998 to the reservoir 1938 defined by the body of the implant 1932. The body of implant 1932 can define channels, either sub-surface or surface channels, running from reservoir 1938 to the exterior surface of implant 1932. The implant 1932 is an orthopaedic implant, such as a prosthesis, a nail, a plate, or an implanted pin of an external fixation device.

d. A drug pump, reservoir, and/or port can be located external to the body and connected to the implant by, for example, a delivery tube or catheter. The main difference between the example of this subparagraph and the example of subparagraph c of this paragraph is that the catheter runs from one location inside the body to another location inside the body in the example of subparagraph c of this paragraph, while the catheter runs from outside of the body to the implant inside the body in the example of this subparagraph. FIG. 29 shows schematically this option for an orthopaedic implant system. According to system 2030, a reservoir 2094, a pump 2095, and a port 2096 are not implanted under the skin of a patient body 2034 but are shown connected to the reservoir 2038 of the implant 2032 by a transcutaneous (passing, entering, or made by penetration through the skin) catheter 2098. The reservoir 2094, pump 2095, and port 2096 are thereby configured for delivering the therapeutic agent (shown by arrow 2036, which also shows the direction of travel of the therapeutic agent) from the reservoir 2094 to the treatment site 2042 via the implant 2032. Stated another way, the pump 2095 and port 2096 can cooperate with the reservoir 2094 to deliver the therapeutic agent 2036 via the catheter 2098 to the reservoir 2038 defined by the body of the implant 2032. The body of implant 2032 can define channels, either sub-surface or surface channels, running from reservoir 2038 to the exterior surface of implant 2032. The implant 2032 is an orthopaedic implant, such as a prosthesis, a nail, a plate, or an implanted pin of an external fixation device.

e. A catheter runs from outside the body to the implant inside the body but would not include a pump, a reservoir, or a port being attached to the outside end of the catheter (the outside end being the end opposite the end which is attached to the implant).

The orthopaedic implants of the present invention can be applied in conjunction with any currently available designs, including porous coatings, and can also be used in conjunction with cemented implants.

The present invention further provides a method of using an orthopaedic implant system, such as system 30. The method includes the steps of: implanting an orthopaedic implant 32 at a selected location within a corporeal body 34, implant 32 including a reservoir 38 and a plurality of channels 40; receiving at least one therapeutic agent 36 in reservoir 38; conveying at least one therapeutic agent 36 from reservoir 38 to a treatment site 42 relative to corporeal body 34 via channels 40; and delivering at least one therapeutic agent 42 to corporeal body 34. As discussed above, the implant according to the present invention is a prosthesis, a nail, a plate, or an external fixation device with an implanted pin. Implant 32 includes a body 44 which is implanted at the selected location, body 44 defining reservoir 38 and channels 40 and including an exterior surface 46, channels 40 fluidly communicating reservoir 38 with exterior surface 46 and thereby conveying therapeutic agent 36 from reservoir 38 to exterior surface 46. The method can include attaching a porous surface 1154 to exterior surface 1146, porous surface 1154 receiving bone and/or tissue ingrowth 1156 therein, porous surface 1154 including a first side 1164 attached to exterior surface 1146 and a second side 1166 opposing first side 1164, porous surface 1154 including a through-hole 1168 running from first side 1164 to second side 1166, through-hole 1168 communicating at least one therapeutic agent 1136 from first side 1164 to second side 1166 and thereby communicating at least one therapeutic agent 1136 to treatment site 1142. Exterior surface 1146 can define a surface channel 1170, surface channel 1170 being in communication with and cooperating with at least one channel 1140 and at least one through-hole 1168 and thereby providing at least one therapeutic agent 1136 from reservoir 1138 to treatment site 1142. At least one channel 40 can be a sub-surface channel 1172, sub-surface channel 1172 and through-hole 1168 being aligned with and cooperating with one another and thereby providing at least one therapeutic agent 1136 from reservoir 1138 to treatment site 1142. The method can include implanting a second reservoir 1994, a pump 1995, and/or a port 1996 in corporeal body 1934 remote from implant 1932, connecting second reservoir 1994, pump 1995, and/or port 1996 to reservoir 1938 of implant 1932 by at least one catheter 1998 implanted in corporeal body 1934, and delivering at least one therapeutic agent 1936 to treatment site 1942 via implant 1932, catheter 1998, and second reservoir 1994, pump 1995, and/or port 1996. The method can include providing a second reservoir 2094, a pump 2095, and/or a port 2096 which is not implanted in corporeal body 2034, connecting second reservoir 2094, pump 2095, and/or port 2096 to reservoir 2038 of implant 2032 by at least one transcutaneous catheter 2098, and delivering at least one therapeutic agent 2036 to treatment site 2042 via implant 2032, catheter 2098, and second reservoir 2094, pump 2095, and/or port 2096. The method can include inserting a cartridge 1586 into reservoir 1538, cartridge 1586 containing at least one therapeutic agent 1536 and releasing at least one therapeutic agent 1536 into reservoir 1538 and/or at least one channel 1540 such that at least one therapeutic agent 1536 moves away from reservoir 1538 in at least one channel 1540, removing cartridge 1586 from reservoir 1538 after implant 1532 has been implanted in corporeal body 1534, and replacing cartridge 1586 with another cartridge 1586 after implant 1532 has been implanted in corporeal body 1534. The method can include providing a spongy element 1892, reservoir 1838 containing spongy element 1892. Body 1644, 1744 of implant 1632, 1732 can be partially or completely porous. External fixation device 1432 can include implantable pin 1476, a sheath 1478 coupled with pin 1476, and reservoir 1480 coupled with sheath 1478, pin 1476 defining a plurality of channels 1440. Implant may include only one reservoir. The method can include refilling reservoir 38 with at least one therapeutic agent 36 after implant 32 has been implanted in corporeal body 34. The method can include delivering a plurality of therapeutic agents 36 to corporeal body 34 via reservoir 38 and channels 40 of implant 32.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic implant system, comprising:
    an external fixation device including an implantable pin, a sheath coupled with said pin, a reservoir coupled with said sheath, and a plurality of channels, said external fixation device being implantable at a selected location within a corporeal body and configured for delivering at least one therapeutic agent to said corporeal body, said reservoir configured for receiving said at least one therapeutic agent, said plurality of channels configured for conveying said at least one therapeutic agent from said reservoir to a treatment site relative to said corporeal body, said pin defining said plurality of channels.

2. The orthopaedic implant system of claim 1, wherein said pin defines said reservoir and includes an exterior surface, said plurality of channels fluidly communicating said reservoir with said exterior surface and thereby being configured for conveying said at least one therapeutic agent from said reservoir to said exterior surface.

3. The orthopaedic implant system of claim 2, further including a porous surface attached to said exterior surface, said porous surface configured for receiving at least one of bone and tissue ingrowth therein, said porous surface including a first side attached to said exterior surface and a second side opposing said first side, said porous surface including a through-hole running from said first side to said second side, said through-hole configured for communicating said at least one therapeutic agent from said first side to said second side and thereby for communicating said at least one therapeutic agent to said treatment site.

4. The orthopaedic implant system of claim 3, further including a surface channel defined by said exterior surface, said surface channel being in communication with and cooperating with one said channel and said through-hole to provide said at least one therapeutic agent from said reservoir to said treatment site.

5. The orthopaedic implant system of claim 3, wherein at least one of said channels is a sub-surface channel, said sub-surface channel and said through-hole being aligned with and cooperating with one another to provide said at least one therapeutic agent from said reservoir to said treatment site.

6. The orthopaedic implant system of claim 2, further including at least one of a second reservoir, a pump, and a port implantable in said corporeal body remote from said external fixation device and connected to said reservoir of said external fixation device by at least one catheter implantable in said corporeal body and thereby configured for delivering said at least one therapeutic agent to said treatment site via said external fixation device.

7. The orthopaedic implant system of claim 2, further including at least one of a second reservoir, a pump, and a port not implantable in said corporeal body but which is connected to said reservoir of said external fixation device by at least one transcutaneous catheter and which is thereby configured for delivering said at least one therapeutic agent to said treatment site via said external fixation device.

8. The orthopaedic implant system of claim 2, further including a cartridge inserted into said reservoir, said cartridge containing said at least one therapeutic agent and being configured for releasing said at least one therapeutic agent into at least one of said reservoir and at least one of said channels such that said at least one therapeutic agent moves away from said reservoir in said at least one channel, said cartridge being removable from said reservoir and replaceable with another cartridge after said external fixation device has been implanted in said corporeal body.

9. The orthopaedic implant system of claim 2, wherein said pin is one of partially porous and completely porous.

10. The orthopaedic implant system of claim 2, wherein said implant includes only one said reservoir.

11. The orthopaedic implant system of claim 2, wherein said reservoir is configured for being refilled with said at least one therapeutic agent after said external fixation device has been implanted in said corporeal body.

12. The orthopaedic implant system of claim 2, wherein said external fixation device is configured for delivering a plurality of therapeutic agents to said corporeal body via said reservoir and said plurality of channels.

13. The orthopaedic implant system of claim 1, further including a spongy element, said reservoir containing said spongy element.

14. A method of using an orthopaedic implant system, said method comprising the steps of:

implanting an orthopaedic implant at a selected location within a corporeal body, said implant including an implantable pin, a sheath coupled with said pin, a reservoir coupled with said sheath, and a plurality of channels, said pin defining said plurality of channels, said pin being implanted at least partially within the corporeal body and said sheath and said reservoir residing at least partially outside the corporeal body when said pin is implanted within the corporeal body;

receiving at least one therapeutic agent in said reservoir;

conveying said at least one therapeutic agent from said reservoir to a treatment site relative to said corporeal body via said plurality of channels; and delivering said at least one therapeutic agent to said corporeal body.

15. The method of claim 14, wherein said pin defines said reservoir and includes an exterior surface, said plurality of channels fluidly communicating said reservoir with said exterior surface and thereby conveying said at least one therapeutic agent from said reservoir to said exterior surface.

16. The method of claim 15, further including attaching a porous surface to said exterior surface, said porous surface receiving at least one of bone and tissue ingrowth therein, said porous surface including a first side attached to said exterior surface and a second side opposing said first side, said porous surface including a through-hole running from said first side to said second side, said through-hole communicating said at least one therapeutic agent from said first side to said second side and thereby communicating said at least one therapeutic agent to said treatment site.

17. The method of claim 14, further including refilling said reservoir with said at least one therapeutic agent.

18. The method of claim 14, further including implanting at least one of a second reservoir, a pump, and a port in said corporeal body remote from said implant, connecting at least one of said second reservoir, said pump, and said port to said reservoir of said implant by at least one catheter implanted in said corporeal body, and delivering said at least one therapeutic agent to said treatment site via said implant, said catheter, and at least one of said second reservoir, said pump, and said port.

19. The method of claim 14, further including providing at least one of a second reservoir, a pump, and a port which is not implanted in said corporeal body, connecting at least one of said second reservoir, said pump, and said port to said reservoir of said implant by at least one transcutaneous catheter, and delivering said at least one therapeutic agent to said treatment site via said implant, said catheter, and at least one of said second reservoir, said pump, and said port.

20. The method of claim 14, further including inserting a cartridge into said reservoir, said cartridge containing said at least one therapeutic agent and releasing said at least one therapeutic agent into at least one of said reservoir and at least one of said channels such that said at least one therapeutic agent moves away from said reservoir in said at least one channel, removing said cartridge from said reservoir after said implant has been implanted in said corporeal body, and replacing said cartridge with another cartridge after said implant has been implanted in said corporeal body.

* * * * *